United States Patent [19]
Resch

[11] Patent Number: 4,886,800
[45] Date of Patent: Dec. 12, 1989

[54] SUBSTITUTED CINNOLINE DERIVATIVES AS CNS DEPRESSANTS

[75] Inventor: James F. Resch, Wilmington, Del.
[73] Assignee: ICI Americas Inc., Wilmington, Del.
[21] Appl. No.: 868,791
[22] Filed: May 29, 1986

[30] Foreign Application Priority Data

May 30, 1985 [GB] United Kingdom ............... 85/13639

[51] Int. Cl.$^4$ ................... A61K 31/535; A61K 31/50; C07D 413/12; C07D 237/28
[52] U.S. Cl. ................................ 514/234.5; 514/248; 544/116; 544/119; 544/235; 548/469; 558/391; 558/445; 564/215; 564/305; 564/442
[58] Field of Search ........................... 514/248, 234.5; 544/235, 116, 119

[56] References Cited

U.S. PATENT DOCUMENTS

| | | | |
|---|---|---|---|
| 3,657,241 | 4/1972 | Kurihara | 544/235 |
| 4,027,023 | 5/1977 | Preston et al. | 544/235 |
| 4,085,103 | 4/1978 | Preston et al. | 544/235 |
| 4,379,929 | 4/1983 | Conrad et al. | 514/960 |
| 4,729,782 | 3/1988 | Labovitz et al. | 544/235 |
| 4,826,837 | 5/1989 | Doria et al. | 514/248 |

FOREIGN PATENT DOCUMENTS

| | | |
|---|---|---|
| 2290209 | 6/1986 | France . |
| 123525 | 1/1977 | German Democratic Rep. . |
| 1306839 | 2/1973 | United Kingdom ................ 544/235 |

OTHER PUBLICATIONS

*The Condensed Chemical Dictionary*, (10th Ed.), Van Nostrand Reinhold Co., Publishers, p. 19 (1981).
*Hackh's Chemical Dictionary*, (4th Ed.), McGraw-Hill Book Co., Publishers, p. 16 (1972).
Patel, J. B. and Malick, J. B., "Effects of Isoproterenol and Chlordiazepoxide on Drinking and Conflict Behaviors in Rats", *Pharmacology Biochemistry & Behavior* (1980), 12: 819–821.
Meiners, B. A. and Salama, A. I., "Enhancement of Benzodiazepine and Gaba Binding By the Novel Anxiolytic, Tracazolate", *Eur. Journal of Pharmacology* (1982), 78: 315–322.
Braestrup, Claus and Squires, Richard F., "Specific benzodiazepine receptors in rat brain characterized by high–affinity [$^3$H]diazepam binding", *Proceedings of the National Academy of Science U.S.A.* (1977) 74: 3805.
Wastek, G. J., Speth, R. C., Reisine, T. D. and Yamamura, H. I., "The Effect of gamma–aminobutyric Acid on $^3$H–Flunitrazepam Binding in Rat Brain", *Eur. Journal of Pharmacology* (1978) 50: 445.
Bylund, D. B., *Receptor Binding Techniques*, Society for Neuroscience (1980), vol. 6, p. 1.
Gassman, Paul G. and Gruetzmacher, Gordon D., "Azasulfonium Salts. Intermediates in a General Procedure for the Alkylation of Aromatic Amines", *J. Amer. Chem. Soc.*, (1974) 96: 5487–5495.
Sikkar, Rein and Martinson, Per, "Synthesis and Dediazoniation of 2-Butyl- and 2,5-Dibutylbenzenediazonium Ions", *Acta Chemica Scandinavica* (1980) B34:551–557.
Chorvat, Robert J., Desai, Bipin N., Radak, Suzanne Evans, McLaughlin, Kathleen T., Miller, James E., Jett, Charlene and Rohrbacher, Elaine, "22-Hydroxycholesterol Derivatives as HMG CoA Reductase Suppressors and Serum Cholesterol Lowering Agents", *Journal of Medicinal Chemistry* (1985) 28: 194–200).
Hayashi, T., et al., *J. Amer. Chem. Soc.* (1984) 106: 158.
Gerlach, H. et al., *Helv. Chim. Acta.* (1977) 60, Fasc. 8: 2860–2865.
Chemical Abstracts, vol. 87 (1977), p. 603, No. 117893f.
Chemical Abstracts, vol. 82, No. 139453m, (1975).

*Primary Examiner*—Anton H. Sutto
*Assistant Examiner*—E. Bernhardt
*Attorney, Agent, or Firm*—Rosemary M. Miano; Thomas E. Jackson

[57] ABSTRACT

The present invention comprises certain amide and ester derivatives of 4-substituted-cinnoline-3-carboxylic acids and 3-acyl-4-substituted-cinnoline derivatives, and their use as central nervous system (CNS) depressants.

9 Claims, No Drawings

SUBSTITUTED CINNOLINE DERIVATIVES AS CNS DEPRESSANTS

BACKGROUND OF THE INVENTION

The present invention comprises certain amide and ester derivatives of 4-substituted-cinnoline-3-carboxylic acids and 3-acyl-4-substituted-cinnoline derivatives, their use as central nervous system (CNS) depressants (especially anxiolytics) and pharmacological tools, methods for their preparation, pharmacetical compositions containing them and intermediates used in their preparation.

Selected cinnoline compounds including selected 4-amino- and 4-oxo-cinnoline-3-carboxamides are disclosed in East German Patent 123525 (Verfahren zur Herstellung von substituierten 4-Aminocinnolinen): U.S. Pat. No. 4,379,929 to Conrad et al; Daunis et al., "Préparation et propriétés de cinnolones-3 et cinnolones-4," *Bull. de la Societe Chimique de France*, 8:3198–3202 (1972); Lunt et al. "A New Cinnoline Synthesis," *J. Chem. Soc.* (C), 687–695 (1968): Gewald, et al., "Synthese von 4-Aminocinnolinen aus (Arylhydrazono) (cyan)-essigsäurederivaten," *Liebigs Ann. Chem.*, 1390–1394 (1984): and U.S. Pat. No. 3,657,241 to Kurihara. Additionally, selected cinnoline compounds, including 3-acyl-4-substituted cinnoline derivatives are disclosed in *Liebigs Ann. Chem.* 1390–1394 (1984) *supra* and Sandison, et al., "A New Heterocyclisation Reaction Leading to Cinnolin-4(1H)-one Derivatives," *J. Chem. Soc. Chem. Comm.*, 752–753 (1974). However, none of the foregoing discloses or suggests the novel compounds of the present invention or suggests their use as CNS depressants.

SUMMARY OF THE INVENTION

The compounds of the present invention are amide and ester derivatives of 4-substituted cinnoline-3-carboxylic acids and 3-acyl-4-substitutedcinnoline derivatives. These compounds have been found to possess utility as anxiolytics in animals. Also included as part of the invention are pharmaceutical compositions containing one or more of the compounds for administration to an animal in need of an anxiety-reducing medication, such a method of treatment, and methods for the synthesis of the compounds as well as novel intermediates used in the syntheses.

DETAILED DESCRIPTION OF THE INVENTION

The compounds of the invention are cinnolines of formula (I) (set out hereinbelow following the Examples with other formulae denoted by Roman numerals) wherein substituents at the 3- to 8-positions, respectively, are respresented by $R^3$ to $R^8$, respectively, and wherein:

$R^3$ is an amide of the formula (II):

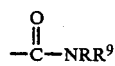

II an ester of the formula (III):

III or a ketone of the formula (IV):

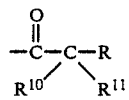

IV $R^4$ is $-NR^{12}R^{13}$ or $-OR^{12}$;

$R^5$, $R^6$, $R^7$ and $R^8$ may be the same or different and are each hydrogen, (1–10C)alkyl, (2–10C)alkenyl, (2–10C)alkynyl, (3–6C)cycloalkyl, (4–10C)cycloalkylalkyl, (1–10C)aryl, (1–10C)substituted aryl, (2–11C)arylalkyl, (2–11C)(substitued aryl)alkyl, (1–10C)fluoroalkyl having at least one fluorine, (2–10C)haloalkenyl having at least one halogen, (2–10C)alkoxyalkyl, (1–10C)hydroxyalkyl, halogeno, (1–10C)alkoxy, (3–10C)alkenyl-oxy, hydroxy, nitro, cyano or amino including substituted amino;

R and $R^9$ may be the same or different and may each be hydrogen (provided that $R^3$ is not an ester of formula III) except that R and $R^9$ cannot both be hydrogen at the same time, (1–10C)alkyl, (3–10C)alkenyl, (3–10C)alkynyl, (3–6C)cycloalkyl, (4–10C) (cycloalkyl), (1–10C)aryl, (1–10C)substituted aryl, (2–11C)arylalkyl, (2–11C)(substituted aryl)alkyl, 4,5-dihydro-2-thiazolyl of formula (V): (2–10C)alkoxyalkyl, (1–10C)hydroxyalkyl, (2–10C)fluoroaelkyl having at least one fluorine provided that no fluorine is on a carbon bonded to a nitrogen, (2–10C)haloalkenyl having at least one halogen provided that no halogen is on a carbon bonded to a nitrogen; or R and $R^9$ when taken together form a (4–6C)alkylene group wherein one of the carbons may optionally be replaced by an oxygen, or, when taken together, form a (4–6C)alkenylene group;

$R^{10}$ and $R^{11}$ may be the same or different and are each hydrogen or (1–4C)alkyl:

$R^{12}$ and $R^{13}$ may be the same or different and are each hydrogen, (1–4C)alkyl, (2–10C)acyl, or (4–10c) cycloalkylalkyl, provided that $R^{12}$ may not be hydrogen when $R^3$ is of formula (III) and $R^4$ is $OR^{12}$; and pharmaceutically acceptable salts and 1- or 2-position N-oxides thereof.

Unless otherwise specified, the alkyls, alkenyls and alkynyls described for this invention may be straight or branched chain. Aryl shall mean an organic radical derived from an aromatic hydrocarbon, e.g., phenyl. Aryl shall also include heterocyclic radicals, e.g., those derived from pyrrole, furan, thiophene, pyridine, thiazole or indole. Substituted amino includes mono- or di-substituted amines. Substituted aryls may be substituted with, for example, (1–4C)alkyl, (1–4C)alkoxy, or halogeno. The number of substitutions on an aryl may vary. For example, where the aryl has only one ring, for example phenyl, the number of substituents may be from 1 to 3. All of the substitutions are taken independently of each other; thus, a three member substitution from a listed group may include three different members, two of the same members or all identical members. The term halogeno includes fluoro, chloro, bromo and iodo. These definitions shall apply throughout this specification except where specifically indicated otherwise.

Particular values for the groups defined above are as follows:

R$^3$ selected from the group consisting of the group as defined above:

R$^4$ selected from the group consisting of —NR$^{12}$R$^{13}$ and OR$^{12}$ in which R$^{12}$ and R$^{13}$ are each independently selected from the group consisting of hydrogen, (1-4C)alkyl, (2-4C)acyl and (4-8C)cycloalkylalkyl;

R$^5$, R$^6$, R$^7$ and R$^8$ (each independently) selected from the group consisting of hydrogen, (1-6C) alkyl, (2-6C)alkenyl, (2-6C)alkynyl, (3-6C)cycloalkyl, (4-8C)cycloalkylalkyl, (2-8C)aryl, (3-9C)arylalkyl, (1-6C)hydroxyalkyl, halogeno, and (1-8C)alkoxy;

R and R$^9$ each independently selected from the group consisting of hydrogen (provided that R$^3$ is not an ester of formula III and further provided that R and R$^9$ are not both hydrogen at the same time), (1-6C)alkyl, (3-6C)alkenyl, (3-6C)alkynyl, (3-6C)cycloalkyl, (4-8C)(cycloalkyl)alkyl, (2-8C)aryl, (3-9C) arylalkyl, 4,5-dihydrothiazol-2-yl, (1-6C)hydroxyalkyl, (2-6C)fluoroalkyl having at least one fluorine (for example, 1-4 fluorines), provided no fluorine is on a carbon bonded to a nitrogen: or R and R$^9$, when taken together, form a (4-6C)-alkylene wherein one of the carbons may optionally be replaced by an oxygen, or when taken together form a (4-6C)alkenylene: and R$^{10}$ and R$^{11}$ each independently selected from the group consisting of hydrogen and (1-4C)alkyl.

More particular values for the above-defined groups are:

R$^3$ is an amide of formula II or a ketone of formula IV;

R$^4$ is —NR$^{12}$R$^{13}$ or OH:

R$^5$, R$^6$ and R$^7$ are each independently selected from the group consisting of hydrogen, (1-5C)alkyl, chloro and methoxy:

R$^8$ is selected from the group consisting of hydrogen, (1-5C)alkyl, (2-4C)alkenyl, (2-5C)alkynyl, (3-6C)cycloalkyl, (4-7C)cycloalkylalkyl, phenyl, phenylmethyl, (1-4C)hydroxyalkyl, and halogeno;

R and R$^9$ are each independently selected from the group consisting of hydrogen, (1-4C)alkyl, (3-4C)alkenyl, (3-4C)alkynyl, (4-5C)cycloalkylalkyl, (2-4C)fluoroalkyl having 1-4 fluoros, 4,5-dihydrothiazol-2-yl, (2-4C)hydroxyalkyl, phenylmethyl, or R and R$^9$ when taken together form a (4-5C)alkylene in which one of the carbons may optionally be replaced by an oxygen, or when taken together form a 4 carbon alkenylene:

R$^{10}$ and R$^{11}$ are each hydrogen:

R$^{12}$ and R$^{13}$ are each independently selected from the group consisting of hydrogen, (1-4C)alkyl, (4-6C)cycloalkylalkyl and (2-4C)acyl.

Even more particular values for some of the groups listed above are as follows: R$^5$=hydrogen or chloro. R$^6$=hydrogen, chloro, methoxy or butyl: R$^7$=hydrogen, chloro, methyl, methoxy or pentyl: R$^8$=hydrogen, fluoro, chloro, bromo, iodo, methyl, ethyl, propyl, butyl, pentyl, methoxy, cyclopropyl, 2-methylpropyl, 3-methylbutyl, cyclopentylmethyl, 3-butenyl, 3-hydroxybutyl, phenyl, phenylmethyl or 3-pentynyl; R=hydrogen, methyl, ethyl, propyl, butyl, cyclopropylmethyl, 2-propenyl or phenylmethyl: R$^9$=methyl, ethyl, propyl, butyl, 2-methylpropyl, cyclopropylmethyl, cyclobutylmethyl 2-propenyl, 2-propynyl, 2-butynyl, propargyl, cyclopropyl, 2,2-trifluoroethyl, phenyl, phenylmethyl, 3-hydroxypropyl, or 4,5 dihydrothiazol-2-yl; R$^{10}$=hydrogen; R$^{11}$=hydrogen: R$^{12}$=hydrogen, butyl, cyclopropylmethyl or butyryl; R$^{13}$=hydrogen.

Preferred compounds are those in which R is hydrogen; R$^3$ is CONRR$^9$; R$^5$ is hydrogen; R$^6$ is hydrogen; R$^7$ is hydrogen or halogen; R$^8$ is (3-5C)alkyl; and R$^9$ is (2-4C)alkyl, (3-4C)alkenyl, or (4-5C)(cycloalkyl) alkyl, e.g., cyclopropylmethyl.

Particularly preferred compounds are 4-amino-N,8-dipropyl-3-cinnolinecarboxamide (Formula I with R$^3$ of Formula II; R$^4$=NH$_2$; R$^5$=R$^6$=R$^7$=H; R$^8$=n-propyl; R=H; R$^9$=n-propyl, (Examples 24 and 51)); 4-amino-8-butyl-N-(2-propenyl)-3-cinnolinecarboxamide (Formula I with R$^3$ of Formula II: R$^4$=NH$_2$; R$^5$=R$^6$=R$^7$=H; R$^8$=n-butyl; R=H; R$^9$=2-propenyl, (Example 17)); 4-amino-8-pentyl-N-(2-propenyl)-3-cinnolinecarboxamide (Formula I with R$^3$ of Formula II; R$^4$=NH$_2$; R$^5$=R$^6$=R$^7$=H; R$^8$=n-pentyl; R=H; R$^9$=2-propenyl, (Examples 1, 14, 29 and 30)); 4-amino-8-butyl-N-cyclopropylmethyl-3-cinnolinecarboxamide (Formula I with R$^3$ of Formula II; R$^4$=NH$_2$; R$^5$=R$^6$=R$^7$=R=H; R$^8$=n-butyl; R$^9$=cyclopropylmethyl (Examples 20, 64, and 65)); 4-amino-N-cyclopropylmethyl-8-propyl-3-cinnolinecarboxamide (Formula I with R$^3$ of Formula II: R$^4$=NH$_2$; R$^5$=R$^6$=R$^7$=R=H: R$^8$=n-propyl; R$^9$=cyclopropylmethyl (Examples 26, 66, and 67)); 4-amino-8-butyl-N-cyclobutylmethyl-3-cinnolinecarboxamide (Formula I with R$^3$ of Formula II; R$^4$=NH$_2$; R$^5$=R$^6$=R$^7$=R=H; R$^8$=n-butyl; R$^9$=cyclobutylmethyl (Example 70)); 4-amino-8-butyl-N-cyclopropyl-3-cinnolinecarboxamide (Formula I with R$^3$ of Formula II; R$^4$=NH$_2$; R$^5$=R$^6$=R$^7$=R=H; R$^8$=n-butyl; R$^9$=cyclopropyl (Example 72); 4-amino-8-(3-methylbutyl)-N-propyl-3-cinnolinecarboxamide (Formula I with R$^3$ of Formula II; R$^4$=NH$_2$; R$^5$=R$^6$=R$^7$=R=H; R$^8$=3-methylbutyl; R$^9$=n-propyl (Example 94)); and 4-amino-8-cyclopentylmethyl-N-propyl-3-cinnolinecarboxamide (Formula I with R$^3$ of Formula II; R$^4$=NH$_2$; R$^5$=R$^6$=R$^7$=H; R$^8$=cyclopentylmethyl; R$^9$=n-propyl (Example 96)).

Most preferred compounds are 4-amino-N-cyclopropylmethyl-8-propyl-3-cinnolinecarboxamide (Formula I with R$^3$ of Formula II; R$^4$=NH$_2$; R$^5$=R$^6$=R$^7$=R=H R$^8$=n-propyl; R$^9$=cyclopropylmethyl (Examples 26, 66, and 67)); and, more especially, 4-amino-8-butyl-N-cyclopropylmethyl-3-cinnolinecarboxamide (Formula I with R$^3$ of Formula II: R$^4$=NH$_2$; R$^5$=R$^6$=R$^7$=R=H; R$^8$=n-butyl; R$^9$=cyclopropylmethyl (Examples 20, 64, and 65)).

The pharmaceutically-acceptable salts of the compounds of formula (I) are, for example, physiologically acceptable acid-addition salts such as mineral acid salts, e.g., hydrohalides, especially hydrochlorides and hydrobromides, sulfates, nitrates and phosphates, or organic acid salts, for examples, methanesulfonates.

Compounds of formula (I) may be prepared by using, in part, methods known in the art. The following processes are provided as further features of the invention:

(a) For those compounds of formula (I) in which R$^3$ is an amide of formula (II) and R$^4$ is NH$_2$, a preferred method is reacting a compound of formula (VI) where A is selected from the group consisting of a carboxylic acid (COOH) or an acid derivative (COOR$^4$) with a displaceable substituent (R$^4$) such as an ester where R$^4$ may be for example (1-6C) alkyl, halogeno, acyloxy, or imidazolyl, acid chloride, anhydride or imidazolide, with an amine of formula NHRR$^9$;

(b) For those compounds of formula (I) in which $R^3$ is an ester of formula (III) and $R^4$ is $NH_2$, reacting a compound of formula (VI) with an alcohol of formula ROH where R is as defined above:

(c) For those compounds of formula (I) in which $R^3$ is a ketone of formula (IV) and $R^4$ is $NH_2$, reacting a nitrile of formula (VII) with an organometallic reagent of formula $RR^{10}R^{11}CMgX$, wherein R, $R^{10}$, and $R^{11}$ are as defined above and X is a halogen, followed by hydrolysis of a resulting intermediate;

(d) For those compounds of formula (I) in which $R^3$ is an amide of formula (II) and $R^4$ is $NH_2$, an alternate method of synthesis comprises reacting a hydrazono-substituted acetamide of formula (VIII) (or its geometric isomer) with a Lewis acid catalyst (for example, and preferably, aluminum chloride or ethylaluminum dichloride) in an inert solvent (for example, toluene, nitrobenzene or chlorobenzene);

(e) For those compounds of formula (I) in which $R^4$ is $NR^{12}R^{13}$ and one or both of $R^{12}$ and $R^{13}$ are alkyl, alkylating a compound of formula (I) in which $R^4$ is $NH_2$;

(f) For those compounds of formula (I) in which $R^4$ is $NR^{12}R^{13}$ and one or both of $R^{12}$ and $R^{13}$ are acyl, acylating a compound of formula (I) in which $R^4$ is $NH_2$;

(g) For those compounds of formula (I) in which $R^4$ is $OR^{12}$, reacting a compound of formula (I) in which $R^4$ is $NH_2$ with a compound of formula $MOR^{12}$ in which M is an alkali metal, or with a compound of formula $L(OR^{12})_2$ in which L is an alkaline earth.

(h) For those compounds of formula (I) in which $R^8$ is, for example, alkyl, alkenyl, alkynyl, cycloakyl, (cycloalkyl)alkyl, aryl, or (aryl)alkyl, reacting an organometallic derivative of the compound $R^8X$ in which X is a halogen (for example, an organozinc or Grignard reagent) with that compound of formula (I) in which $R^8$ is initially chlorine, bromine, or iodine, in the presence of a suitable transition metal catalyst (for example, dichloro[1,1'-bis(diphenylphosphino)ferrocene]palladium (II)).

When a compound of the invention is obtained as a free base and a salt is desired or required, the base may be further reacted with an acid to afford a pharmaceutically acceptable anion.

Also, it may be desired to optionally use a protecting group during all or portions of the above described processes; for example, when $R^8$=hydroxyalkyl, it is appropriate to use a protecting group (see Example 98). The protecting group may then be removed when the final compound is to be formed.

The starting material of formula (VI) for use in processes (a) and (b) may be prepared by hydrolysis of an amide of formula (IX). The amide of formula (IX) may be prepared by reaction of a hydrazono-substituted acetamide of formula (X). (or its geometric isomer) with a Lewis acid catalyst (for example, and preferably, aluminum chloride or ethylaluminum dichloride) in an inert solvent (such as toluene, nitrobenzene, or chlorobenzene). The compound of formula (X) (or its geometric isomer) may be prepared by diazotizing of an aniline of formula (XI), followed by coupling of the intermediate diazonium ion with 2-cyanoacetamide.

The starting material of formula (VII) for process (c) may be prepared by reaction of a hydrazono-substituted propanedinitrile of formula (XII), with a Lewis acid (such as aluminum chloride) in an inert solvent (such as chlorobenzene). The compound of formula (XII) may be prepared by diazotization of an aniline of formula (XI) followed by coupling of the intermediate diazonium ion with malononitrile.

The starting material of formula (VIII) for process (d) may be prepared by diazotization of an aniline of formula (XI) followed by coupling of the intermediate diazonium ion with an N-substituted-2-cyanoacetamide of formula (XIII). The compound of formula (XIII), if not itself known, may be prepared by the reaction of an amine of formula $NHRR^9$ with ethyl 2-cyanoacetate, optionally in the presence of a solvent such as diethyl ether.

Compositions, especially pharmaceutical compositions, of the invention may be prepared and used according to methods known for the compounds cartazolate and tracazolate. Specifically, the new compounds of this invention are central nervous system depressants and may be used as tranquilizers or ataractic agents for the relief of anxiety and tension states, for example, in mice, cats, rats, dogs and other mammalian species such as man, in the same manner as chlordiazepoxide. For this purpose a compound or mixture of compounds of formula (I), or non-toxic physiologically acceptable salts, such as acid addition salts thereof, may be administered orally or parenterally in a conventional dosage form such as tablet, pill, capsule, injectable or the like. The dosage in mg/kg of body weight of compounds of the present invention in mammals will vary according to the size of the animal and particularly with respect to the brain/body weight ratio. In general, a higher mg/kg dosage for a small animal such as a dog will have the same effect as a lower mg/kg dosage in an adult human. A minimum effective dosage for a compound of formula (I) will be at least about 0.1 mg/kg of body weight per day for mammals with a maximum dosage for a small mammal such as a dog, of about 100 mg/kg per day. For humans, a dosage of about 0.1 to 12 mg/kg per day will be effective, for example, about 5 to 600 mg/day for an average man. The dosage can be given once daily or in divided doses, for example, 2 to 4 doses daily, and such dosage will depend on the duration and maximum level of activity of a particular compound. The dose may be conventionally formulated in an oral or parenteral dosage form by compounding about 5 to 250 mg per unit of dosage of conventional vehicle, excipient, binder, preservative, stabilizer, flavor or the like as called for by accepted pharmaceutical practice, for example, as described in U.S. Pat. No. 3,755,340. The compounds of this invention may be used in pharmaceutical compositions comprising a compound of formula (I) as previously described or be contained in the same formulation with or co-administered with one or more known drugs.

Among the tests conducted to demonstrate the anxiolytic activity of the present compounds is the Shock-Induced Suppression of Drinking (Rats) (SSD) Test, described in *Pharmacology Biochemistry & Behavior*, (1980), 12:819–821 which is carried out as follows:

Male Wistar rats in the weight range of 200 to 220 grams are deprived of water for 48 hours and deprived of food for 24 hours before testing. Normally the rats are orally intubated (5 ml/kg) with the test compound at dosage levels of 0.20, 0.39, 0.78, 1.56, 3.125, 6.25, 12.5, 25 and 50 mg/kg body weight. (The test compound is administered intraperitoneally in a few instances). The vehicle control group of rats is also intubated by mouth. A positive control group of rats is also orally administered a control dose of 18 mg/kg of chlordiazepoxide. Random selection of the rats is utilized in dosing. The rats are returned to the cage for one hour. Sixty minutes after drug administration, the rat is quietly removed from its cage and the hind feet wiped with Signa electrode gel made by Parker Laboratories of Orange, N.J. When intraperitoneal (i.p.) administration is used, the protocol is identical except that the drugs are administered (with selected concentrations in volumes of 5 ml/kg) 30 minutes prior to testing. Dosages are varied by varying the concentration of drug in the 5 ml volume. The rat is placed on the floor in the chamber facing a licking tube. The animal is allowed 5 minutes to make 20 licking responses and receive the first shock (0.5 mA). If this response does not occur, the animal is removed and eliminated from the study. If 20 licking responses are made, the animal is permitted an additional 3 minutes during which time each 20th lick is paired with a 0.5 mA shock. This period is automatically started, counted and terminated. The number of licks and shocks are recorded. The activity of the compound tested is evaluated by comparing the mean shocks of the group dosed with the test compound to the mean shocks of the vehicle group via a Students' t-test. In general, an increase in the number of shocks received compared to the control is indicative of the anti-conflict or anti-anxiety activity of the compound. The difference is regarded as statistically significant if the probability p that the difference is due to chance in the Students' t-test is less than 0.05.

A second test for anxiolytic activity conducted on compounds of the invention is the [$^3$H]flunitrazepam binding test described in the *European Journal of Pharmacology*, (1982), 78:315–322, by B. A. Meiners and A. I. Salama, which is conducted as follows:

A lysed mitochondrial-synaptosomal (P$_2$) fraction was prepared from the cerebral cortex of male Sprague-Dawley rats weighing 150–250 g, according to the method of Braestrup and Squires in the *Proceedings of the National Academy of Science U.S.A.*, (1977) 74:3805. The fraction was then washed twice by centrifugation in 50 millimolar Tris-Citrate pH 7.4 buffer containing 100 millimolar NaCl.

Specific flunitrazepam binding was measured by a filtration assay similar to that of Wastek et al. in the *European Journal of Pharmacology*, (1978), 50:445. The 2 ml assays contained 0.2 nM [$^3$H]flunitrazepam (84 Curie/mmol) and membranes equivalent to 10 mg fresh weight (0.2 mg protein) in 50 millimolar Tris-Citrate pH 7.4 buffer containing 100 millimolar NaCl. Drugs were added in 20 μ l of 95% ethanol which was also added to the control. Non-specific binding was determined in the presence of 2.5 μM clonazepam or 0.5 μM flunitrazepam. The samples were allowed to equilibrate for 90 min. at 0° C. before being filtered and rinsed. Typical assays were done in triplicate. That concentration of test compound causing 50% displacement of [$^3$H]flunitrazepam relative to a control that contains no added test compound, defined as IC$_{50}$, may be determined from the data for a number of concentrations (ranging from about 0.05 to about 500 nanomolar) of test compound using a logit transformation of the data as described by D. B. Bylund in *Receptor Binding Techniques*, published by Society for Neuroscience (1980).

Anxiolytic activity is indicated in the flunitrazepam binding test by a displacement of the flunitrazepam such as is exhibited by benzodiazepines or by enchancement of the binding such as is shown by cartazolate and tracazolate.

Compounds of the invention tested showed activity in one or both of the above described tests. In the SSD test a compound was judged active if it were effective at a dose of 50 mg/kg given i.p. (intraperitoneally) or p.o. (orally). In the [$^3$H]flunitrazepam test a compound was judged active if it showed 50% or more displacement of specific [$^3$H]flunitrazepam binding at a tested concentration of 500 nanomolar or less.

Compounds of this invention have not exhibited toxicological problems.

The following examples describe synthesis of compounds of the invention, with all temperatures being in degrees Celsius (C) and the following abbreviations being used: mg (milligrams), kg (kilograms); , g (grams), w or wt (weight), v (volume), mM (millimoles), ml (milliliters), mm (millimeters), M (molar), N (normal), m.p. (melting point), bp (boiling point), tlc (thin layer chromatography), NMR (nuclear magnetic resonance), $^1$H NMR (Proton Nuclear Magnetic Resonance), ppm (parts per million downfield from tetrametylsilane), s (singlet), d (doublet), t (triplet), m (multiplet), q (quartet), br. (broad), DMF (dimethyl formamide), HOAc (acetic acid), THF (tetrahydrofuran), recryst. (recrystallization), ND (not determined), mTorr (10$^{-3}$ Torr, with 1 Torr=133.3 Pascals as a conversion factor). Note that when substitutions are made as for example in "following the procedure in Example X, but replacing Y" it is to be understood that an approximately equal molar amount of the substituted material was used. All chemical symbols have their usual meanings unless otherwise indicated.

It is to be understood that generic terms such as "(1–10C)alkyl" include both straight and branched chain alkyl radicals but references to individual alkyl radicals such as "propyl" include only the straight chain ("normal") radical, branched chain isomers such as "isopropyl" being specifically referred to. Unless otherwise stated, solvent ratios are specified using a volume/volume basis.

EXAMPLE 1 a. 4-Amino-8-pentyl-N-(2-propenyl)-3-cinnolinecarboxamide (Formula I, $R^3$=CONRR$^9$, $R^4$=NH$_2$, $R^5$=$R^6$=$R^7$=R=H, $R^8$=pentyl, $R^9$=2-propenyl)

To a suspension of 4-amino-8-pentyl-3-cinnolinecarboxylic acid (2.46 g) in dry DMF (100 ml) was added 1,1'-carbonyldiimidazole (1.69 g). The mixture was stirred under nitrogen at room temperature for one hour. 2-Propenylamine (0.61 g) was then added and the mixture was stirred an additional two hours. The resulting solution was poured into water (200 ml) and the product extracted with two portions of ethyl acetate (100 ml each). The combined organic extracts were washed with water and then brine, and finally dried (MgSO$_4$). Evaporation furnished 2.42 g (85% yield) of the title product as an off-white solid. Recrystallization from toluene/hexane furnished an analytical sample of white crystals, m.p. 122.5°–124°. $^1$H NMR (CHCl$_3$-d): 0.89 (t, 3H), 1.32–1.48 (m, 4H), 1.83 (t of q, 2H), 3.41 (t, 2H), 4.16 (br. t, 2H), 5.20 (d, 1H), 5.30 (d, 1H), 5.98 (m, 1H), 7.55–7.73 (m, 3H), 8.68 (br. t, exchangeable, 1H) ppm. Calculated for C$_{17}$H$_{22}$N$_4$O: C, 68.43; H, 7.43; N, 18.70. Found: C, 68.73: H, 7.41; N, 18.74.

b. 2-Cyano-2-[(2-pentylphenyl)hydrazono]acetamide (Formula X, $R^5$=$R^6$=$R^7$=H, $R^8$=pentyl)

To a solution of 2-pentylaniline (2.65 g) in HOAc (10 ml) was added water (5 ml) and concentrated hydrochloric acid (5 ml). The solution was cooled to −5° with stirring, resulting in a white crystalline suspension. To this mixture was added dropwise a solution of sodium nitrite (1.17 g) in water (6 ml), maintaining the internal temperature below 5°. The resulting clear yellow solution was stirred an additional ten minutes at −5°, and was then added to a solution of 2-cyanoacetamide (4.1 g) in water (165 ml) containing sodium acetate (22 g) which had been chilled to 0°. This mixture was stirred mechanically at 0° for 1 hour, and was then diluted with water (150 ml). After 10 minutes, the precipitated solid was collected by filtration and the filtrate set aside. The solid was washed with water and then with hexane, and was dried in vacuo. Additional product which precipitated from the filtrate on standing at room temperature was similarly collected, washed, and dried. There was thus obtained 2.76 grams (66% yield) of title product as a mixture of (E)- and (Z)-isomers. Recrystallization of a small sample from ethyl acetate/hexane produced an analytical sample of the (E)-isomer as yellow crystals, m.p. 141°–143.5°. Calculated for $C_{14}H_{18}N_4O$: C, 65.09; H, 7.02; N, 21.68. Found: C, 65.27; H, 6.92; N, 21.72.

c. 4-Amino-8-pentyl-3-cinnolinecarboxamide (Formula IX, $R^5=R^6=R^7=H$, $R^8=$pentyl)

To a suspension of the product of Example 1(b) (2.76 g) in dry toluene (50 ml) was added aluminum chloride (3.54 g). The mixture was stirred under nitrogen at 100° for one hour. The reaction mixture was then cooled to room temperature, diluted with ethyl acetate (200 ml), and stirred while water was added cautiously until no further precipitate appeared. The mixture was then stirred with aqueous sodium hydroxide (200 ml of 10% w/v solution) for 30 minutes. The aqueous layer was separated and discarded, leaving a suspension of the product in the organic phase. The suspension was then shaken with aqueous sodium hydroxide (100 ml of 10% w/v solution) and water (100 ml) in succession and these aqueous layers were discarded. The organic phase was diluted with hexane (200 ml) and chilled to 0°. The precipitated white solid was collected by filtration providing 2.02 grams (73% yield) of title product. Recrystallization from ethanol furnished an analytical sample of white crystals, m.p. 229°–231°. Calculated for $C_{14}H_{18}N_4O$: C, 65.09; H, 7.02; N, 21.68. Found: C, 64.87; H, 7.06: N, 21.63.

d. 4-Amino-8-pentyl-3-cinnolinecarboxylic acid (Formula VI, $R^5=R^6=R^7=H$, $R^8=$pentyl, A=COOH)

To a suspension of 2.0 g of the product of Example 1(c) in ethanol (100 ml) was added aqueous sodium hydroxide (20 ml of 10% w/v solution). The mixture was heated to reflux with stirring for 16 hours. The solution was cooled to room temperature and treated with HOAc until pH 4 was reached. The resulting slurry was chilled to 0° and then filtered, providing a white solid which was washed with water and then dried in vacuo. 1.5 Grams (75% yield) of title product was obtained. Recrystallization from ethanol provided an analytical sample of white crystals, m.p. 208°–210°. Calculated for $C_{14}H_{17}N_3O_2$: C, 64.85; H, 6.61; N, 16.20. Found: C, 64.59; H, 6.63; N, 16.01.

EXAMPLES 2–13

Following the procedures given in Examples 1(a)–(d), but replacing the 2-propenylamine (used in step (a) to make the appropriate substitutions at R and $R^9$) with the appropriate amine, more compounds of Formula I were prepared ($R^3=$CONRR$^9$, $R^4=$NH$_2$, $R^5=R^6=R^7=$H, $R^8=$pentyl, and R and $R^9$ as listed in Table I). Examples 2–13 are listed in Table I.

TABLE I

| Example | R | $R^9$ | Yield | Melting Point (recryst. solvent) | Formula | Calculated | | | Found | | |
|---|---|---|---|---|---|---|---|---|---|---|---|
| | | | | | | C | H | N | C | H | N |
| 2* | CH$_3$ | 2-propenyl | 58% | 77–79° (toluene/hexane) | C$_{18}$H$_{24}$N$_4$O | 69.20 | 7.44 | 17.93 | 69.60 | 7.74 | 18.00 |
| 3* | CH$_3$ | 2-propynyl | 30% | 107–108.5° (ethyl acetate/hexane) | C$_{18}$H$_{22}$N$_4$O | 68.65 | 7.14 | 18.05 | 69.77 | 7.28 | 17.98 |
| 4* | CH$_3$ | propyl | 66% | 75.5–79° (ethyl ether/hexane) | C$_{18}$H$_{26}$N$_4$O | 68.76 | 8.33 | 17.82 | 68.68 | 8.28 | 17.82 |
| 5* | H | ethyl | 47% | 107–109° (ethyl ether/hexane) | C$_{16}$H$_{22}$N$_4$O | 67.10 | 7.74 | 19.56 | 67.34 | 8.00 | 19.51 |
| 6 | H | butyl | 80% | 120–121.5° (toluene/hexane) | C$_{18}$H$_{26}$N$_4$O | 68.76 | 8.33 | 17.81 | 68.60 | 8.30 | 17.67 |
| 7* | H | 2,2,2-trifluoroethyl | 42% | 130–133° (toluene) | C$_{16}$H$_{19}$N$_4$OF$_3$·H$_2$O | 53.63 | 5.91 | 15.63 | 53.58 | 5.57 | 15.43 |
| 8 | H | phenylmethyl | 60% | 128–130° (toluene/hexane) | C$_{21}$H$_{24}$N$_4$O | 72.39 | 6.94 | 16.07 | 72.36 | 7.04 | 16.18 |
| 9* | H | phenyl | 40% | 170–171° (toluene/hexane) | C$_{20}$H$_{22}$N$_4$O | 71.83 | 6.63 | 16.75 | 71.97 | 6.55 | 16.88 |
| 10* | H | 2-butynyl | 50% | 117–118.5° (ethyl acetate/hexane) | C$_{18}$H$_{22}$N$_4$O | 69.65 | 7.14 | 18.05 | 69.40 | 7.16 | 17.69 |
| 11 | H | 2-hydroxypropyl | 60% | 111–112° (toluene) | C$_{17}$H$_{24}$N$_4$O$_2$ | 64.53 | 7.64 | 17.71 | 64.40 | 7.60 | 17.68 |
| 12 | H | 2-(4,5-dihydrothiazolyl) | 53% | 211–212° (ethyl acetate) | C$_{17}$H$_{21}$N$_5$OS | 59.45 | 6.16 | 20.39 | 59.39 | 6.13 | 20.07 |
| 13 | H | 2-propynyl | 59% | 127.5–129.5° (ethyl ether/hexane) | C$_{17}$H$_{20}$N$_4$O·1/3H$_2$O | 67.53 | 6.89 | 18.53 | 67.47 | 6.98 | 18.52 |

*Notes:
Example 2: Reaction temperature raised to 50° after addition of amine.
Example 3: Reaction temperature raised to 40° after addition of amine; reaction time 3 hours.
Example 4: Reaction time 16 hours.
Example 5: Reaction temperature lowered to 0° while gaseous amine was bubbled into mixture.
Example 7: Reaction Reaction time 80 hours.
Example 9: Reaction temperature raised to 80° after addition of amine; reaction time 12 hours.
Example 10: 2-Butynylamine may be prepared by a method of Marszak-Fleury, A., Bull. de la Societe Chimique de France, pp. 480–483 (1958).

EXAMPLE 14

4-Amino-8-pentyl-N-(2-propenyl)-3-cinnolinecarboxamide (Formula I, $R^3$=CONRR$^9$, $R^4$=NH$_2$, $R^5$=$R^6$=$R^7$=R=H, $R^8$=pentyl, $R^9$=2-propenyl)

An alternative method of preparing the compound of Example 1(a) is described as follows. To a suspension of 4-amino-8-pentyl-3-cinnolinecarboxylic acid (1.08 g) in dry DMF (25 ml) was added 2-propenylamine (0.24 g) and diphenylphosphoryl azide (1.15 g). After cooling to −5°, triethylamine (0.42 g) was added, and the mixture was stirred under nitrogen for two hours. After warming to room temperature overnight, the mixture was diluted with water (100 ml) and the product was extracted into ethyl acetate (100 ml). The organic phase was washed with water (100 ml) and then with brine (100 ml) and finally dried (MgSO$_4$). Evaporation left a solid which was purified by flash chromatography over silica gel, eluting with 2:1 (v/v) hexane/ethyl acetate. Recrystallization from toluene/ hexane provided the title compound as 0.43 gram (35% yield) of white crystals, m.p. 124°–125°. Calculated for $C_{17}H_{22}N_4O$: C, 68.48; H, 7.43; N, 18.70. Found: C, 68.60; H, 7.40; N, 18.84.

EXAMPLE 15

4-Amino-8-pentyl-N-(2-propynyl)-3-cinnolinecarboxamide (Formula I, $R^3$=CONRR$^9$, $R^4$=NH$_2$, $R^5$=$R^6$=$R^7$=R=H, $R^8$=pentyl, $R^9$=2-propynyl)

An alternative method of preparing the compound of Example 13 is as follows. The procedure of Example 14 was employed, substituting 2-propynylamine for 2-propenylamine. The title compound was obtained as white crystals in 38% yield, m.p. 129°–130°. $^1$H NMR (CHCl$_3$-d, characteristic peaks only): 2.28 (t, 1H), 4.31 (d of d, 2H), 8.73 (br. t, exchangeable, 1H) ppm. Calculated for $C_{17}H_{20}N_4O$: C, 68.90; H, 6.80; N, 18.90. Found: C, 68.66; H, 6.68; N, 18.73.

EXAMPLE 16

4-Amino-N-methyl-8-pentyl-N-propyl-3-cinnolinecarboxamide (Formula I, $R^3$=CONRR$^9$, $R^4$=NH$_2$, $R^5$=$R^6$=$R^7$=H, $R^8$=pentyl, $R^9$=propyl, R=methyl)

An alternative method of making the compound of Example 4 is as follows. The procedure of Example 14 was employed, substituting N-methyl-N-propylamine for the 2-propenylamine. The title compound was obtained as a white solid in 39% yield and was analytically identical in all respects to the title compound obtained in Example 4.

EXAMPLE 17 a. 4-Amino-8-butyl-N-(2-propenyl)-3-cinnolinecarboxamide (Formula I, $R^3$=CONRR$^9$, $R^4$=NH$_2$, $R^5$=$R^6$=$R^7$=R=H, $R^8$=butyl, $R^9$=2-propenyl)

The procedure of Example 1(a) was employed, substituting 4-amino-8-butyl-3-cinnolinecarboxylic acid for 4-amino-8-pentyl-3-cinnolinecarboxylic acid. The crude product was purified by flash chromatography over silica gel, eluting with hexane/ethyl acetate (1:1 v/v). Recrystallization from toluene/hexane furnished the title compound as white crystals in 69% yield, m.p. 126°–127°. $^1$H NMR (CHCl$_3$-d, characteristic peaks only): 4.15 (br. t, 2H), 5.20 (d, 1H), 5.33 (d, 1H), 5.96 (m, 1H), 8.68 (br. t, exchangeable, 1H). Calculated for $C_{16}H_{20}N_4O$: C, 67.58; H, 7.08; N, 19.70. Found: C, 67.39; H, 7.23; N, 19.60.

b. 2-[(2-Butylphenyl)hydrazono]-2-cyanoacetamide (Formula X, $R^5$=$R^6$=$R^7$=H, $R^8$=butyl)

Following the procedure of Example 1(b), but substituting 2-butylaniline for 2-pentylaniline, and maintaining the internal temperature below −10° during the addition of the sodium nitrite solution, a 75% yield of the product was obtained as a mixture of (E)- and (Z)-isomers. Recrystallization from ethyl acetate/hexane provided an analytical sample, m.p. 130°–138°. Calculated for $C_{13}H_{16}N_4O$: C, 63.92; H, 6.60: N, 22.93. Found: C, 63.77; H, 6.73; N, 22.84.

c. 4-Amino-8-butyl-3-cinnolinecarboxamide (Formula IX, $R^5$=$R^6$=$R^7$=H, $R^8$=butyl)

Following the procedure of Example 1(c), but substituting 2-[(2-butylphenyl)hydrazono]-2-cyanocetamide for 2-cyano-2-[(2-pentylphenyl)hydrazono]acetamide, there was obtained 86% yield of the title product.

Recrystallization from ethanol provided an analytical sample, m.p. 215°–217.5°. Calculated for $C_{13}H_{16}N_4O$: C, 63.92; H, 6.60; N, 22.93. Found: C, 63.61; H, 6.48; N, 22.45 d. 4-Amino-8-butyl-3-cinnolinecarboxylic acid (Formula VI, with $R^5$=$R^6$=$R^7$=H, $R^8$=butyl, A=COOH)

Following the procedure of Example 1(d), but substituting 4-amino-8-butyl-3-cinnolinecarboxamide for 4-amino-8-penyyl-3-cinnolinecarboxamide, there was obtained 61% yield of the title product. Recrystallization from ethanol provided an analytical sample, m.p. 218°–220°. Calculated for $C_{13}H_{15}N_3O_2$: C, 63.65; H, 6.16; N, 17.13, Found: C, 63.23; H, 6.14; N, 16.70.

EXAMPLES 18–22

Following the procedures given in Examples 17(a)–(d), but replacing the 2-propenylamine (used in step (a) to make the appropriate substitutions at R and $R^9$) with the appropriate amine, more compounds of Formula I were prepared ($R^3$=CONRR$^9$, $R^4$=NH$_2$, $R^5$=$R^6$=$R^7$=H, $R^8$=butyl, and R and $R^9$ as listed in Table II). Examples 18–22 are listed in Table II.

TABLE II

| Example | R | $R^9$ | Yield | Melting Point (recryst. solvent) | Formula | Calculated | | | Found | | |
|---|---|---|---|---|---|---|---|---|---|---|---|
| | | | | | | C | H | N | C | H | N |
| 18 | H | propyl | 63% | 112–113° (toluene/hexane) | $C_{16}H_{22}N_4O$ | 67.11 | 7.74 | 19.56 | 67.22 | 7.88 | 19.68 |
| 19 | H | butyl | 59% | 121–122° (toluene/hexane) | $C_{17}H_{24}N_4O$ | 67.97 | 8.05 | 18.65 | 68.04 | 8.20 | 18.66 |
| 20 | H | cyclopropyl-methyl | 73% | 123.5–125° (toluene/hexane) | $C_{17}H_{22}N_4O$ | 68.43 | 7.43 | 18.78 | 68.69 | 7.41 | 18.73 |
| 21 | H | propargyl | 57% | 159–160° (toluene/hexane) | $C_{16}H_{18}N_4O$ | 68.06 | 6.43 | 19.84 | 68.32 | 6.38 | 19.77 |

TABLE II-continued

| Example | R | $R^9$ | Yield | Melting Point (recryst. solvent) | Formula | Calculated C | H | N | Found C | H | N |
|---|---|---|---|---|---|---|---|---|---|---|---|
| 22* | H | ethyl | 56% | 129–130° (toluene/hexane) | $C_{15}H_{20}N_4O$ | 66.15 | 7.40 | 20.57 | 66.06 | 7.40 | 20.46 |

*Notes:
Example 22: Reaction temperature was lowered to 0° while gaseous amine was bubbled into reaction mixture.

EXAMPLE 23 a. 4-Amino-N-(2-propenyl)-8-propyl-3-cinnolinecarboxamide (Formula I, $R^3$=CONRR$^9$, $R^4$=NH$_2$, $R^5$=$R^6$=$R^7$=R=H, $R^8$=propyl, $R^9$=2-propenyl)

The procedure of Example 1(a) was employed, substituting 4-amino-8-propyl-3-cinnolinecarboxylic acid for 4-amino-8-pentyl-3-cinnolinecarboxylic acid. The crude product was purified by flash chromatography over silica gel, eluting with hexane/ethyl acetate (1:1 v/v). Recrystallization from toluene/hexane furnished 74% yield of the title compound as white crystals, m.p. 115°–117°. $^1$H NMR (CHCl$_3$-d, characteristic peaks only): 4.16 (br. t, 2H), 5.21 (d, 1H), 5.34 (d, 1H), 5.96 (m, 1H), 8.68 (br. t, exchangeable, 1H).

Calculated for $C_{15}H_{18}N_4O$: C, 66.65; H, 6.71; N, 20.73, Found: C, 66.73; H, 6.71; N, 20.6.

b. 2-Cyano-2-[(2-propylphenyl)hydrazono]acetamide (Formula X, $R^5$=$R^6$=$R^7$=H, $R^8$=propyl)

Following the procedure of Example 1(b) but substituting 2-propylaniline for 2-pentylaniline, and maintaining the internal temperature below −12° during the addition of the sodium nitrite solution, there was obtained 89% yield of the title product as a mixture of (E)- and (Z)-isomers. Recrystallization from ethyl acetate/hexane provided an analytical sample of the (E)-isomer, m.p. 128°–130°.

Calculated for $C_{12}H_{14}N_4O$: C, 62.59; H, 6.13; N, 24.33, Found: C, 62.56; H, 6.16; N, 24.37, c. 4-Amino-8-propyl-3-cinnolinecarboxamide (Formula IX, $R^5$=$R^6$=$R^7$=H, $R^8$=propyl)

Following the procedure of Example 1(c), but substituting 2-cyano-2-[(2-propylphenyl)hydrazono]acetamide for 2-cyano-2-[(2-pentylphenyl)hydrazono]acetamide, 81% yield of the product was obtained. Recrystallization from ethanol furnished an analytical sample as white crystals, m.p. 249°–250°.

Calculated for $C_{12}H_{14}N_4O$: C, 62.59; H, 6.13; N, 24.33, Found: C, 62.31; H, 6.30; N, 23.47, d. 4-Amino-8-propyl-3-cinnolinecarboxylic acid (Formula VI, $R^5$=$R^6$=$R^7$=H, $R^8$=propyl, A=COOH)

Following the procedure of Example 1(d), but substituting 4-amino-8-propyl-3-cinnolinecarboxamide for 4-amino-8-pentyl-3-cinnolinecarboxamide, 62% yield of the product was obtained. Recrystallization from ethanol furnished an analytical sample as white crystals, m.p. 216°–218°.

Calculated for $C_{12}H_{13}N_3O_2 \cdot \frac{1}{2}H_2O$: C, 59.99; H, 5.87; N, 17.49, Found C, 59.35; H, 5.54; N, 17.16,

EXAMPLES 24–28

Following the procedures given in Example 23(a)–(d), but substituting the appropriate amine for the 2-propenylamine (used in part (a) to make the appropriate substitutions at R and $R^9$), more compounds of Formula I were prepared ($R^3$=CONRR$^9$, $R^5$=$R^6$=$R^7$=R=H, $R^4$=NH$_2$, $R^8$=propyl, and R and $R^9$ as listed in Table III). Examples 24–28 are listed in Table III.

TABLE III

| Example | R | $R^9$ | Yield | Melting Point (recryst. solvent) | Formula | Calculated C | H | N | Found C | H | N |
|---|---|---|---|---|---|---|---|---|---|---|---|
| 24 | H | propyl | 70% | 117.5–119° (ethyl ether/hexane) | $C_{15}H_{20}N_4O$ | 66.15 | 7.40 | 20.57 | 66.20 | 7.32 | 20.57 |
| 25 | H | butyl | 68% | 117–119° (toluene/hexane) | $C_{16}H_{22}N_4O$ | 67.11 | 7.74 | 19.56 | 67.21 | 7.79 | 19.65 |
| 26 | H | cyclopropylmethyl | 68% | 121–122.5° (toluene/hexane) | $C_{16}H_{20}N_4O$ | 67.58 | 7.09 | 19.70 | 67.55 | 6.98 | 19.58 |
| 27 | H | propargyl | 66% | 145–149° (toluene) | $C_{15}H_{16}N_4O$ | 67.15 | 6.01 | 20.88 | 66.86 | 6.28 | 20.64 |
| 28* | H | ethyl | 41% | 139–140° (CH$_2$Cl$_2$/hexane) | $C_{14}H_{18}N_4$ | 65.09 | 7.02 | 21.69 | 65.29 | 7.13 | 21.47 |

*Notes:
Example 28: Reaction temperature lowered to 0° while gaseous amine was bubbled into reaction mixture.

EXAMPLE 29 a. 4-Amino-8-pentyl-N-(2-propenyl)-3-cinnolinecarboxamide (Formula I, $R^3$=CONRR$^9$, $R^4$=NH$_2$, $R^5$=$R^6$=$R^7$=R=H, $R^8$=pentyl, $R^9$=2-propenyl)

A third way of preparing the compound of Example 1(a) is as follows. To a solution of (Z)-2-cyano-2-[(2-pentylphenyl)hydrazono]-N-(2-propenyl)acetamide (1.2 g) in nitrobenzene (20 ml) was added aluminum chloride (1.6 g), and the stirred mixture was warmed to 40°–50° under nitrogen for 16 hours. Upon cooling to room temperature, the mixture was diluted with ethyl acetate (100 ml) and then chilled to 0°. Aqueous sodium hydroxide (100 ml) of 10% w/v solution) was added and stirring was continued at 0° for one hour. The organic phase was separated, washed with aqueous sodium hydroxide (50 ml of 10% w/v solution), water (50 ml) and brine (50 ml) in succession, and finally dried (MgSO$_4$) Evaporation provided a reddish liquid which was concentrated by Kugelrohr distillation. The oily residue was purified by flash chromatography over silica gel, eluting first with dichloromethane to remove residual nitrobenzene. Elution with dichloromethane/acetonitrile (99:1) provided the title compound as 0.70 g (58% yield) of a white solid. Recrystallization from toluene/hexane provided an analytical sample identical in all respects to that obtained in Example 1(a).

b. (Z)-2-Cyano-2-[(2-pentylphenyl)hydrazono]-N-(2-propenyl)acetamide (Formula VIII, $R^5=R^6=R^7=R=H$, $R^9$=2-propenyl)

A solution of 2-pentylaniline (1.63 g) in HOAc (7 ml) containing water (3.5 ml) was cooled to 0° and concentrated hydrochloric acid (3.5 ml) was added, producing a slurry of white crystals. To this mixture was added dropwise a solution of sodium nitrite (0.94 g) in water (4 ml), with cooling at such a rate as to maintain the internal temperature below 10°. After the addition was completed the clear yellow solution was stirred at 0° for ten minutes and then added cautiously to a stirred mixture of 2-cyano-N-2-propenylacetamide* (1.36 g), sodium acetate (7.0 g), ethanol (35 ml), and aqueous sodium carbonate (70 ml of 1.0 molar solution) which had been previously chilled to 0°. Gas was evolved. The resulting slurry was stirred for 2 hours at 0°, then diluted with water (100 ml) and extracted with ethyl acetate (200 ml). The organic phase was separated, washed with water (100 ml) and then brine (100 ml) and finally dried MgSO$_4$). Evaporation left a solid which was purified by flash chromatography over silica gel, eluting first with hexane to remove nonpolar impurities. *Prepared by reaction of ethyl cyanoacetate with 2-propenylamine according to the general procedure of Shukla, J. S. et al. *Journal of the Indian Chemical Society,* (1978) 55:281-283) (m.p. 60°-62°). Elution with ethyl ether/hexane (1:1 v/v) provided a crude product which was recrystallized from hexane to provide 1.24 g (42% yield) of product as yellow needles, m.p. 81.5°-83°.

Calculated for $C_{17}H_{22}N_4O$: C, 68.43; H, 7.43; N, 18.78, Found: C, 68.48; H, 7.12; N, 18.88,

EXAMPLE 30

4-Amino-8-pentyl-N-(2-propenyl)-3-cinnolinecarboxamide (Formula I, $R^3$=CONRR$^9$, $R^4$=NH$_2$, $R^5=R^6=R^7=R=H$, $R^8$=pentyl, $R^9$=2-propenyl)

A fourth way of preparing the compound of Example 1(a) is as follows. To a stirred suspension of 2-cyano-2-[(2-pentylphenyl)hydrazono]-N-(2-propenyl)acetamide (0.30 g) in dry toluene (4.0 ml) was added a solution of ethylaluminum dichloride in toluene (2.2 ml of 25 wt. % solution) and the resulting mixture was heated to 80° under nitrogen for one hour. Upon cooling, the mixture was diluted with ethyl acetate (50 ml) and was stirred with aqueous sodium hydroxide (50 ml of 10% w/v solution). After 30 minutes the phases were separated and the organic phase was washed with aqueous sodium hydroxide (50 ml of 10% w/v solution), water (50 ml) and brine (50 ml), in succession, and was finally dried (MgSO$_4$). Evaporation provided a yellow solid which was purified by flash chromatography over silica gel, eluting with ethyl acetate/hexane (1:1 v/v). There was thus obtained 0.03 gram (10% yield) of the title compound as a white solid, which analytically identical to the product of Example 1(a).

EXAMPLE 31 a. 4-Amino-N-cyclopropylmethyl-8-pentyl-3-cinnolinecarboxamide (Formula I, $R^3$=CONRR$^9$, $R^4$=NH$_2$, $R^5=R^6=R^7=R=H$, $R^8$=pentyl, $R^9$=cyclopropylmethyl)

To a vigorously stirred suspension of 2-cyano-N-cyclopropylmethyl-2-[(2-pentylphenyl)hydrazono]acetamide (1.3 g) in dry toluene (20 ml) was added aluminum chloride (1.2 g). The mixture was heated under nitrogen to 70° for 3 hours. The mixture was then cooled to room temperature, diluted with ethyl acetate (100 ml) and stirred while water was added in a dropwise manner until no further precipitate formed. Aqueous sodium hydroxide (100 ml of 10% w/v solution) was added and the stirring was continued until all solids had dissolved. The organic layer was separated and washed with aqueous sodium hydroxide (50 ml of 10% w/v solution), water (50 ml), and brine (50 ml) in succession, and finally dried (MgSO$_4$). Evaporation of the solvent provided a crude product which was purified by flash chromatography over silica gel, eluting with hexane/ethyl acetate (4:1 v/v). There was thus obtained 0.91 g (70% yield) of the title compound. Recrystallization from toluene/hexane furnished an analytical sample as white crystals, m.p. 125°-126°. $^1$H NMR (CHCl$_3$-d, characteristic peaks only): 0.31 (m, 2H), 0.58 (m, 2H), 1.10 (m, 1H), 3.39 (m, 2H), 8.70 (br. t, 1H, exchangeable) ppm.

Calculated for $C_{18}H_{24}N_4O$: C, 69.20; H, 7.74; N, 17.93, Found: C, 69.00: H, 7.71; N, 17.80, b. 2-Cyano-N-cyclopropylmethylacetamide (Formula XIII, R=H, $R^9$=cyclopropylmethyl)

Aminomethylcyclopropane (4.9 g) was chilled to 0° and stirred rapidly while ethyl cyanoacetate (3.8 g) was added in a dropwise manner. The mixture was stirred at 0° for 2 hours, and then diluted with diethyl ether (30 ml) and hexane (30 ml). On continued stirring the product deposited as white crystals, which were collected by filtration, washed with hexane, and dried. The title product was obtained as 3.54 g (78% yield) of white crystals, m.p. 66°-68°.

Calculated for $C_7H_{10}N_2O$: C, 60.85; H, 7.29; N, 20.27, Found: C, 60.73; H, 7.40; N, 20.27, c. 2-Cyano-N-cyclopropylmethyl-2-[(2-pentylphenyl)hydrazono]acetamide (Formula VIII, $R^5=R^6=R^7=R=H$, $R^8$=pentyl, $R^9$=cyclopropylmethyl)

A solution of 2-pentylaniline (1.5 g) in HOAc (8 ml) containing H$_2$O (7 ml) was chilled to 0° while concentrated hydrochloric acid (5 ml) was added. An additional portion of water (10 ml) was then added to facilitate efficient stirring of the resulting slurry. A solution of sodium nitrite (0.76 g) in water (5 ml) was added at such a rate as to maintain the internal temperature below 5°. The resulting yellow solution was stirred at 0° for 30 minutes, and was then added to a solution of 2-cyano-N-cyclopropylmethylacetamide (1.4 g) in water (60 ml) containing sodium carbonate (6.4 g), sodium acetate (6.0 g) and ethanol (30 ml) which solution had been previously chilled to 0°. Gas was evolved. After stirring for one hour, the mixture was diluted with water (100 ml) and extracted with ethyl acetate (200 ml). The organic layer was separated, washed with water (100 ml) and brine (100 ml) in succession, and finally dried (Na$_2$SO$_4$). Evaporation provided an orange solid which was recrystallized from ethyl acetate/hexane to provide 2.0 grams (70% yield) of the title product as a yellow solid as a mixture of (E)- and (Z)-isomers, m.p. 102°-104°.

Calculated for $C_{18}H_{24}N_4O$: C, 69.20; H, 7.74; N, 17.93, Found: C, 69.04; H, 7.68; N, 17.91,

EXAMPLE 32 a. 4-Amino-8-chloro-N-(2-propenyl)-3-cinnolinecarboxamide (Formula I, $R^3$=CONRR$^9$, $R^4$=NH$_2$, $R^5$=$R^6$=$R^7$=R=H, $R^8$=Cl, $R^9$=2-propenyl)

To a stirred suspension of 2-[(2-chlorophenyl)hydrazono]-2-cyano-N-(2-propenyl)acetamide (0.60 g) in dry toluene (14 ml) was added a solution of ethylaluminum dichloride in hexane (7.0 ml of 1.0 molar solution) and the resulting mixture was heated under nitrogen to 90° for 26 hours. Upon cooling, the mixture was diluted with ethyl acetate (100 ml) and was stirred with aqueous sodium hydroxide (100 ml of 10% w/v solution). After 30 minutes, the phases were separated and the aqueous layer was again extracted with ethyl acetate (100 ml). The combined organic layers were washed with aqueous sodium hydroxide (50 ml of 10% w/v solution) and then twice with brine (50 ml each). After drying (MgSO$_4$), evaporation furnished a yellow solid which was purified by flash chromatography over silica gel. After elution with hexane/ethyl acetate (3:1 v/v) to remove nonpolar impurities, the product was eluted with hexane/ethyl acetate (1:1 v/v) and was then recrystallized from ethyl acetate/hexane. There was thus obtained 0.14 gram (23% yield) of the title compound as white crystals, m.p. 244°–246°. $^1$H NMR (CHCl$_3$-d, characteristic peaks only): 4.16 (br. t, 2H), 5.21 (d, 1H), 5.33 (d, 1H), 5.98 (m, 1H), 8.65 (br. s, exchangeable, 1H).

Calculated for C$_{12}$H$_{11}$N$_4$OCl.¼H$_2$O: C, 53.94; H, 4.34; N, 20.97. Found: C, 53.92; H, 4.11; N, 20.78.

b. 2-[(2-Chlorophenyl)hydrazono]-2-cyano-N(-2-propenyl)acetamide (Formula VIII, $R^5$=$R^6$=$R^7$=R=H, $R^8$=Cl, $R^9$=2-propenyl)

A mixture of HOAc (9.0 ml), water (4.5 ml), and concentrated hydrochloric acid (4.5 ml) was heated to 90° with vigorous stirring, and 2-chloroaniline (1.92 g) was added. On rapid cooling to 0°, a slurry of white crystals formed. This was stirred rapidly with cooling while a solution of sodium nitrite (1.09 g) in water (5 ml) was added at such a rate as to maintain the internal temperature below 7°. The resulting yellow solution was added to a stirred solution of 2-cyano-N-(2-propenyl)acetamide (2.23 g) in water (100 ml) containing ethanol (50 ml) and sodium acetate (20 g), which solution had been previously chilled to 0°. After stirring for 1½ hours, the precipitate which formed was collected by filtration, washed with water, and dried. There was thus obtained 3.11 grams (79% yield) of title product as a mixture of (E)- and (Z)-isomers. Recrystallization from ethyl acetate/hexane provided an analytical sample of the (Z)-isomer as light orange crystals, m.p. 170°–171.5°.

Calculated for C$_{12}$H$_{11}$N$_4$OCl: C, 54.87; H, 4.22; N, 21.33. Found: C, 54.97; H, 4.31; N, 21.15.

EXAMPLE 33 a. 4-Amino-8-chloro-N-propyl-3-cinnolinecarboxamide (Formula I, $R^3$=CONRR$^9$, $R^4$=NH$_2$, $R^5$=$R^6$=$R^7$=R=H, $R^8$=Cl, $R^9$=propyl)

To a suspension of 2-[(2-chlorophenyl)hydrazono]-2-cyano-N-propylacetamide (9.0 g) in dry toluene (204 ml) was added aluminum chloride (13.6 g) and the mixture was heated to 90° and stirred under nitrogen for 2½ hours. Upon cooling to room temperature, the mixture was diluted with dichloromethane (1 liter) and chilled to 0° with stirring. Water was added dropwise until no further precipitate appeared; aqueous sodium hydroxide (500 ml of 20% w/v solution) was then added and the mixture was stirred for 1 hour. The phases were separated and the aqueous layer was again extracted with dichloromethane (250 ml). The combined organic extracts were washed with brine (250 ml), dried (MgSO$_4$), and evaporated to afford a solid which was purified by filtration of its ethyl acetate solution through a plug of silica gel. Evaporation gave a light tan solid which was recrystallized from ethyl acetate to provide 6.98 g (78% yield) of the title compound as white crystals. A second recrystallization from ethyl acetate provided an analytical sample of white crystals, m.p. 221°–222.5°. $^1$H NMR (CHCl$_3$-d, characteristic peaks only): 1.03 (t, 3H), 1.70 (d of q, 2H), 3.49 (d of t, 2H), 8.58 (br s., exchangeable, 1H).

Calculated for C$_{12}$H$_{13}$N$_4$OCl: C, 54.45; H, 4.95; N, 21.17. Found: C, 54.37; H, 5.13; N, 21.15.

b. (Z)-2-[(2-Chlorophenyl)hydrazono]-2-cyano-N-propylacetamide (Formula VIII, $R^5$=$R^6$=$R^7$=R=H, $R^8$=Cl, $R^9$=propyl)

The procedure of Example 32(b) was employed, substituting 2-cyano-N-propylacetamide* for 2-cyano-N-(2-propenyl)acetamide. There was thus obtained an 88% yield of analytically pure title compound, m.p. 160°–164°, as a yellow solid.

Calculated for C$_{12}$H$_{13}$N$_4$OCl C, 54.45; H, 4.95; N, 21.17. Found: C, 54.30; H, 4.98; N, 21.23.

*Prepared according to Shukla, J. S. et al. *Journal of the Indian Chemical Society*, (1978) 55:281-283 (m.p. 48.5°–50°).

EXAMPLES 34(a)–51(a)

Following the procedure of Example 33(a) for reaction of the appropriate 2-cyano-N-propyl-2-[(substituted-phenyl)hydrazono]acetamide with aluminum chloride, compounds of Formula I ($R^3$=CONRR$^9$, $R^4$=NH$_2$, $R^5$=R=H, $R^9$=propyl and $R^6$, $R^7$ and $R^8$ as listed on Table IV) were prepared as listed in Table IV.

TABLE IV

| Example | $R^6$ | $R^7$ | $R^8$ | Yield | Melting Point (recryst. solvent) | Formula | Calculated C | H | N | Found C | H | N |
|---|---|---|---|---|---|---|---|---|---|---|---|---|
| 34(a) | H | Cl | Cl | 82% | 269–270° (ethyl/acetate) | C$_{12}$H$_{12}$N$_4$OCl$_2$ | 48.18 | 4.04 | 18.73 | 48.02 | 3.82 | 18.74 |
| 35(a) | H | H | Br | 63% | 207–208° (ethyl acetate) | C$_{12}$H$_{13}$N$_4$OBr | 46.62 | 4.24 | 18.12 | 46.56 | 4.28 | 18.09 |
| 36(a) | H | H | I | 45% | 191–194° (methanol/water) | C$_{12}$H$_{13}$N$_4$OI.¼H$_2$O | 39.96 | 3.77 | 15.53 | 39.91 | 3.84 | 15.45 |
| 37(a) | H | H | F | 60% | 242.5–243.5° (ethyl acetate) | C$_{12}$H$_{13}$N$_4$OF | 58.06 | 5.28 | 22.67 | 58.16 | 5.37 | 22.60 |
| 38(a)* | OCH$_3$ | H | H | 65% | 189.5–191° (ethyl acetate) | C$_{13}$H$_{16}$N$_4$O$_2$ | 60.00 | 6.20 | 21.53 | 60.00 | 6.26 | 21.36 |
| 39(a) | H | CH$_3$ | H | 74% | 206–208° | C$_{13}$H$_{16}$N$_4$O | 63.92 | 6.60 | 22.93 | 63.99 | 6.63 | 22.81 |

TABLE IV-continued

| Example | $R^6$ | $R^7$ | $R^8$ | Yield | Melting Point (recryst. solvent) | Formula | Calculated C | H | N | Found C | H | N |
|---|---|---|---|---|---|---|---|---|---|---|---|---|
| 40(a) | H | OCH₃ | H | 24% | (toluene) 248-249° | $C_{13}H_{16}N_4O_2$ | 60.00 | 6.20 | 21.53 | 59.85 | 6.48 | 21.11 |
| 41(a) | H | H | OCH₃ | 15% | (toluene) 228-229° | $C_{13}H_{16}N_4O_2$ | 60.00 | 6.20 | 21.53 | 59.75 | 6.11 | 21.32 |
| 42(a) | H | H | CH₃ | 72% | (toluene) 166.5-168° | $C_{13}H_{16}N_4O$ | 63.92 | 6.60 | 22.93 | 64.05 | 6.63 | 22.82 |
| 43(a) | H | H | ethyl | 78% | (toluene) 135-136.5° | $C_{14}H_{18}N_4O$ | 65.09 | 7.02 | 21.69 | 65.14 | 7.04 | 21.52 |
| 44(a)* | Cl | H | H | 71% | (ethyl acetate) 254.5-255° | $C_{12}H_{13}N_4OCl$ | 54.44 | 4.95 | 21.17 | 54.04 | 4.76 | 20.87 |
| 45(a) | H | Cl | H | 50% | (ethyl acetate) 251-252.5° | $C_{12}H_{13}N_4OCl$ | 54.44 | 4.95 | 21.17 | 54.44 | 4.97 | 21.36 |
| 46(a)* | H | pentyl | H | 48% | (toluene/hexane) 173-174.5° | $C_{17}H_{24}N_4O$ | 67.97 | 8.05 | 18.65 | 68.07 | 8.16 | 18.75 |
| 47(a)* | H | H | pentyl | 77% | (toluene/hexane) 123-125° | $C_{17}H_{24}N_4O$ | 67.97 | 8.05 | 18.65 | 68.03 | 8.15 | 18.61 |
| 48(a)* | butyl | H | H | 77% | (toluene/hexane) 172.5-174° | $C_{16}H_{22}N_4O$ | 67.11 | 7.74 | 19.56 | 66.86 | 7.84 | 19.51 |
| 49(a)* | H | H | H | 73% | (toluene) 185.5-187° | $C_{12}H_{14}N_4O$ | 62.59 | 6.13 | 24.33 | 62.57 | 6.08 | 24.17 |
| 50(a)* | H | H | butyl | 72% | (toluene/hexane) 111-112.5° | $C_{16}H_{22}N_4O$ | 67.11 | 7.74 | 19.56 | 66.89 | 7.97 | 19.27 |
| 51(a)* | H | H | propyl | 89% | (ethyl ether/hexane) 117.5-118° | $C_{15}H_{20}N_4O$ | 66.15 | 7.40 | 20.57 | 66.0 | 7.39 | 20.88 |

*Notes:
Example 38: Nitrobenzene employed in places of toluene as reaction solvent.
Example 44: Reaction temperature 120°.
Example 46: Reaction run at room temperature for 5 hours.
Example 47: Reaction run at room temperature for 16 hours.
Example 48: Reaction run at room temperature for 16 hours.
Example 49: Reaction temperature 75°.
Example 50: Alternative method for product prepared in Example 18 may also be used.
Example 51: Alternative method for product prepared in Example 24 may also be used.

EXAMPLES 34(b)-51(b)

To obtain the required starting materials for Examples 34(a)-51(a), the procedure of Example 33(b) was employed, substituting the appropriate aniline* for 2-chloroaniline. The 2-cyano-N-propyl-2-[(substituted-phenyl)hydrazono]acetamides, compounds of Formula VIII, ($R^5$=R=H, $R^9$=propyl, and $R^6$, $R^7$ and $R^8$ as listed in Table V) were obtained as mixtures of (E)- and (Z)-isomers.

*All of the anilines used in Examples 34(b)-51(b) were commercially available except for 2-pentylaniline, 2-butylaniline and 3-pentylaniline. 2-Pentylaniline and 2-butylaniline may be made by methods well documented in the literature for example see P. G. Gassman et al., *J. Amer. Chem. Soc.*, (1974) 96:5487-95; R. Sikkar et al. *Acta Chemica Scandinavica*, (1980) B34:551-557 respectively. 3-Pentylaniline may be made as follows: to a suspension of butyltriphenylphosphonium bromide (8.0 g) in diethyl ether (120 ml) was added dropwise a solution of butyllithium in hexane (14.4 ml of 1.53 molar solution) with stirring under nitrogen. The resulting dark orange solution was stirred at room temperature for two hours at which time a solution of 3-nitrobenzaldehyde (3.32 g) in diethyl ether (50 ml) was added dropwise resulting in discharge of the orange color. After stirring for 15 hours, the mixture was filtered through a pad of silica gel and the filtrate was evaporated to dryness. The residual liquid was purified by distillation at 66.7 Pascals (500 mTorr), providing 1.37 grams (36% yield) of 1-nitro-3-(2-pentenyl)benzene boiling over a range of 80°-90° (bath temperature). Repetition of this procedure furnished additional material. Without further purification, 2.75 grams of this 1-nitro-3-(2-pentenyl)benzene was dissolved in ethanol (50 ml) and placed in a hydrogenation bottle along with approximately 10 grams of Raney nickel which had been washed with ethanol. The mixture was shaken under a positive pressure of hydrogen (about 241,500 Pascals, 35 pounds per square inch gauge reading) at room temperature for two hours, and was then filtered. Evaporation of the solvent provided a liquid residue which was distilled at 66.7 Pascals (500 mTorr), providing 1.7 grams (72% yield) of 3-pentylaniline boiling at 120° (bath temperature).

TABLE V

| Example | $R^8$ | $R^7$ | $R^6$ | Yield | Melting Point (recryst. solvent) | Formula | Calculated C | H | N | Found C | H | N |
|---|---|---|---|---|---|---|---|---|---|---|---|---|
| 34(b) | Cl | Cl | H | 84% | 200.5-202° (ethyl acetate/hexane) | $C_{12}H_{12}N_4OCl_2$ | 48.18 | 4.04 | 18.73 | 48.09 | 3.97 | 18.63 |
| 35(b) | Br | H | H | 93% | 158-160° (ethyl acetate/hexane) | $C_{12}H_{13}N_4OBr$ | 46.62 | 4.24 | 18.12 | 46.61 | 4.23 | 18.20 |
| 36(b) | I | H | H | 95% | 187° (ethanol/water) | $C_{12}H_{13}N_4OI$ | 40.47 | 3.68 | 15.73 | 40.37 | 3.58 | 15.62 |
| 37(b) | F | H | H | 29% | 148-151° (toluene/hexane) | $C_{12}H_{13}N_4OF$ | 58.06 | 5.28 | 22.67 | 58.47 | 5.42 | 22.09 |
| 38(b) | H | H | OCH₃ | 77% | 165-167.5° (ethyl acetate) | $C_{13}H_{16}N_4O_2$ | 60.00 | 6.20 | 21.53 | 59.95 | 6.14 | 21.53 |
| 39(b) | H | CH₃ | H | 36% | 172-174° (ethyl acetate) | $C_{13}H_{16}N_4O$ | 63.92 | 6.60 | 22.93 | 63.78 | 6.75 | 22.76 |
| 40(b) | H | OCH₃ | H | 32% | 115.5-117° (ethyl ether/hexane) | $C_{13}H_{16}N_4O_2$ | 60.00 | 6.20 | 21.53 | 60.00 | 6.23 | 21.40 |
| 41(b) | OCH₃ | H | H | 45% | 177-180° (ethyl acetate/hexane) | $C_{13}H_{16}N_4O_2$ | 60.00 | 6.20 | 21.53 | 60.07 | 6.16 | 21.33 |
| 42(b) | CH₃ | H | H | 59% | 134-136° (ethyl ether/hexane) | $C_{13}H_{16}N_4O$ | 63.92 | 6.60 | 22.93 | 63.88 | 6.55 | 22.75 |

TABLE V-continued

| Example | $R^8$ | $R^7$ | $R^6$ | Yield | Melting Point (recryst. solvent) | Formula | Calculated C | H | N | Found C | H | N |
|---|---|---|---|---|---|---|---|---|---|---|---|---|
| 43(b) | ethyl | H | H | 56% | 146–147.5° (ethyl ether/hexane) | $C_{14}H_{18}N_4O$ | 65.09 | 7.02 | 21.69 | 65.31 | 6.99 | 21.59 |
| 44(b) | H | H | Cl | 30% | 173–174° (ethyl acetate/hexane) | $C_{12}H_{13}N_4OCl$ | 54.44 | 4.95 | 21.17 | ND | ND | ND |
| 45(b) | H | Cl | H | 87% | 192–195° (ethyl acetate/hexane) | $C_{12}H_{13}N_4OCl$ | 54.44 | 4.95 | 21.17 | ND | ND | ND |
| 46(b) | H | pentyl | H | 68% | 133–136° (ethyl acetate/hexane) | $C_{17}H_{24}N_4O$ | 67.97 | 8.05 | 18.65 | ND | ND | ND |
| 47(b) | pentyl | H | H | 79% | 94–96° (hexane) | $C_{17}H_{24}N_4O$ | 67.97 | 8.05 | 18.65 | ND | ND | ND |
| 48(b) | H | H | butyl | 26% | 183–185° ($CH_2Cl_2$/hexane) | $C_{16}H_{22}N_4O$ | 67.11 | 7.74 | 19.56 | ND | ND | ND |
| 49(b) | H | H | H | 58% | 160–167° ($CH_2Cl_2$/hexane) | $C_{12}H_{14}N_4O$ | 62.59 | 6.13 | 24.33 | ND | ND | ND |
| 50(b) | butyl | H | H | 26% | ND | $C_{16}H_{22}N_4O$ | 67.11 | 7.74 | 19.56 | ND | ND | ND |
| 51(b) | propyl | H | H | 28% | 106–108° (hexane) | $C_{15}H_{20}N_4O$ | 66.15 | 7.40 | 20.57 | 66.33 | 7.43 | 20.78 |

EXAMPLES 52

4-Hydroxy-N,8-dipropyl-3-cinnolinecarboxamide (Formula I, $R^3$=CONRR$^9$, $R^4$=OH, $R^5$=$R^6$=$R^7$=R=H, $R^8$=propyl, $R^9$=propyl)

To a solution of a portion of the title 4-amino product of Example 24 (0.64 g) in absolute ethanol (20 ml) was added solid potassium hydroxide (3.22 g). The mixture was heated to reflux with stirring under nitrogen for 42 hours. On cooling to room temperature, the mixture was diluted with water (50 ml) and stirred with ethyl ether (50 ml). The organic layer was separated and then discarded. The aqueous phase was treated with acetic acid until pH 6.0 was reached: the precipitate which deposited on cooling to 0° was collected by filtration and washed with water. The precipitate was then dissolved in boiling methanol (250 ml) and evaporated onto flash silica gel (12 g). This was loaded atop a column of flash silica gel (40 g) in chloroform, and the product was eluted with chloroform/methanol (93:7 v/v). The resulting white solid was recrystallized by slow evaporation of a methanol solution, providing the title compound, 0.15 g (23% yield) as a white solid, m.p. 241°–245°. $^1$H NMR (DMSO-d$_6$, characteristic peaks only): 3.32 (d of t, 2H), 7.51 (d of d, 1H), 7.73 (d, 1H), 8.09 (d, 1H), 9.69 (t, exchangeable, 1H), 10.87 (s, exchangeable, 1H) ppm.

Calculated for $(C_{15}H_{19}N_3O)_2$: C, 65.91; H, 7.01; N, 15.37. Found: C, 65.77; H, 7.11; N, 15.34.

EXAMPLE 53

4-Amino-N,8-dipropyl-3-cinnolinecarboxamide hydrochloride salt (Formula I, $R^3$=CONRR$^9$, $R^4$=NH$_2$, $R^5$=$R^6$=$R^7$=R=H, $R^8$=propyl, $R^9$=propyl, hydrochloride salt)

To a solution of a portion of the product of Example 24 (0.55 g) in ethyl ether (50 ml) was added an ethereal solution of hydrogen chloride until no further precipitate formed. The mixture was cooled to 0° and then filtered, washing the collected solid with ethyl ether. There was thus obtained 0.59 gram (95% yield) of the title compound as a white solid, m.p. 215°–233° (with decomposition).

Calculated for $C_{15}H_{20}N_4O\cdot HCl$: C, 58.34; H, 6.85; N, 18.14. Found: C, 57.95; H, 6.92; N, 17.93.

EXAMPLE 54 a. 1-(4-Amino-8-pentylcinnolin-3-yl)-1-pentanone (Formula I, $R^3$=COCR$^{10}$R$^{11}$R, $R^4$=NH$_2$, $R^5$=$R^6$=$R^7$=$R^{10}$=$R^{11}$=H, $R^8$=pentyl, R=propyl)

To a stirred solution of 4-amino-8-pentyl-3-cinnolinecarbonitrile (0.5 g) in dry THF (10 ml) was added a solution of butylmagnesium chloride in THF (2.0 ml of 2.6 molar solution) and the mixture was heated to reflux under nitrogen for 3 hours. The mixture was cooled to room temperature and poured into aqueous hydrochloric acid (60 ml of 10% w/v solution), and the resulting mixture was again heated to reflux for 1.5 hours. Upon cooling, this mixture was poured into saturated aqueous sodium bicarbonate (50 ml) and stirred with ethyl acetate (400 ml) while aqueous sodium hydroxide (10% w/v solution) was added until the aqueous layer was strongly basic. The phases were separated, and the aqueous layer was extracted with ethyl acetate (200 ml). The combined organic layers were dried (Na$_2$SO$_4$) and evaporated to provide a solid which was recrystallized twice from ethyl ether to provide 0.38 g (61% yield) of the title compound as white crystals, m.p. 121.5°–123°. $^1$NMR (CHCl$_3$-d, characteristic peaks only): 0.89 (t, 3H), 0.97 (t, 3H), 3.45 (t, 2H), 3.54 (t, 2H) ppm.

Calculated for $C_{18}H_{25}N_3O$: C, 72.21; H, 8.42; N, 14.03. Found: C, 71.94; H, 8.32; N, 13.91.

b. [(2-Pentylphenyl)hydrazono]propanedinitrile (Formula XII, $R^5$=$R^6$=$R^7$=H, $R^8$=pentyl)

The procedure of Example 29(b) was followed, substituting malononitrile for 2-cyano-N-(2-propenyl)acetamide, and maintaining an internal temperature below 0° during the addition of the sodium nitrite solution. The product precipitated from the reaction mixture and was collected by filtration, washed with water, and dried. Chromatographic purification was unnecessary. The product was obtained as 95% yield of a yellow solid, m.p. 49°–50°.

c. 4-Amino-8-pentyl-3-cinnolinecarbonitrile (Formula VII, $R^5$=$R^6$=$R^7$=H, $R^8$=pentyl)

To a stirred mixture of aluminum chloride (31.1 g) and chlorobenzene (290 ml) was added [(2-pentylphenyl)hydrazono]propanedinitrile (14.0 g) and the mixture was heated to reflux under nitrogen for four hours. Upon cooling, the mixture was poured into ice (1.5 liters) and stirred for one hour. The mixture was treated with aqueous sodium hydroxide (10% w/v) until basic, and then extracted four times with chloroform (500 ml each). The combined chloroform extracts were dried (MgSO$_4$) and evaporated to provide a solid which was purified by flash chromatography over silica gel. Elution with chloroform/ethyl acetate (90:10 and 85:15, v/v) provided 6.0 grams (43% yield) of the title compound. Recrystallization from chloroform provided an analytical sample, m.p. 200°–201°.

Calculated for C$_{14}$H$_{16}$N$_4$: C, 69.97; H, 6.71; N, 23.31. Found: C, 69.69; H, 6.75; N, 23.35.

EXAMPLES 55–59

The procedures of Examples 54(a)–(c) were used to make more compounds of Formula I except that the appropriate Grignard reagent* was used instead of butylmagnesium chloride so that R had the value as shown in Table VI. Compounds of Formula I as listed in Table VI were obtained (R$^3$=COCR$^{10}$R$^{11}$R, R$^4$=NH$_2$, R$^5$=R$^6$R$^7$=R$^{10}$=R$^{11}$=H, R$^8$=pentyl and R as listed in Table VI):

*If not themselves commercially available, the Grignard reagents were generated by reaction of equimolar amounts of magnesium metal turnings with the appropriate alkyl halide in THF for 2 hours. With the exception of 2-(bromoethyl)cyclopropane (which may be prepared according to Chorvat, R. J. et al., *Journal of Medicinal Chemistry*, (1985) 28:194–200), these alkyl halides were commercially available.

vided an analytical sample of white crystals, m.p. 129°–130°. $^1$H NMR (DMSO-d$_6$, characteristic peaks only): 0.94 (t, 3H), 0.98 (t, 3H), 3.31 (t, 2H), 3.38 (t, 2H) ppm.

Calculated for C$_{16}$H$_{21}$N$_3$O: C, 70.82; H, 7.80; N, 15.48. Found: C, 71.03; H, 8.00; N, 15.55.

b. [(2-Propylphenyl)hydrazono]propanedinitrile (Formula XII, R$^5$=R$^6$=R$^7$=H, R$^8$=propyl)

The procedure of Example 54(b) was followed, substituting 2-propylaniline for 2-pentylaniline, and maintaining an internal temperature below −10° during the addition of the sodium nitrite solution. The product was obtained as 97% yield of a yellow solid, m.p. 64.5°–65.5°.

c. 4-Amino-8-propyl-3-cinnolinecarbonitrile (Formula VII, R$^5$=R$^6$=R$^7$=H, R$^8$=propyl)

The procedure of Example 54(c) was followed, substituting [(2-propylphenyl)hydrazono]propanedinitrile for [(2-pentylphenyl)hydrazono]propanedinitrile. The product was obtained as 35% yield. Recrystallization from chloroform furnished an analytical sample of white crystals, m.p. 205°–205.5°.

Calculated for C$_{12}$H$_{12}$N$_4$: C, 67.91; H, 5.70; N, 26.40. Found: C, 67.84; H, 5.69; N, 26.31.

EXAMPLE 61–63

TABLE VI

| Example | R | Yield | Melting Point (recryst. solvent) | Formula | Calculated C | H | N | Found C | H | N |
|---|---|---|---|---|---|---|---|---|---|---|
| 55* | ethyl | 86% | 154–155° (CH$_2$Cl$_2$) | C$_{17}$H$_{23}$N$_3$O | 71.55 | 8.12 | 14.72 | 71.00 | 8.16 | 14.78 |
| 56* | butyl | 80% | 124–125° (CH$_2$Cl$_2$/hexane) | C$_{19}$H$_{27}$N$_3$O | 72.81 | 8.68 | 13.41 | 72.52 | 8.43 | 13.39 |
| 57* | phenylmethyl | 55% | 153–154° (CH$_2$Cl$_2$/hexane) | C$_{22}$H$_{25}$N$_3$O | 76.05 | 7.25 | 12.09 | 76.09 | 7.66 | 11.98 |
| 58* | 2-propenyl | 89% | 128–129° (CH$_2$Cl$_2$) | C$_{18}$H$_{23}$N$_3$O | 72.20 | 7.79 | 14.13 | 72.69 | 7.34 | 14.40 |
| 59* | cyclopropylmethyl | 98% | 143–144° (CH$_2$Cl$_2$) | C$_{19}$H$_{25}$N$_3$O | 73.28 | 8.09 | 13.49 | 73.51 | 8.04 | 13.82 |

*Notes:
Example 55–59: Reaction time reduced from 3 hours to 1 hour prior to pouring reaction onto ice.
Examples 55, 58 and 59: Reaction product purified by flash chromatography over silica gel, eluting with CH$_2$Cl$_2$.

EXAMPLE 60 a. 1-(4-Amino-8-propylcinnolin-3-yl)-1-pentanone (Formula I, R$^3$=COCR$^{10}$R$^{11}$R, R$^4$=NH$_2$, R$^5$=R$^6$32 R$^7$=R$^{10}$=R$^{11}$=H, R$^8$=propyl, R=propyl)

The procedure of Example 54(a), was used except that 4-amino-8-propyl-3-cinnolinecarbonitrile was substituted for 4-amino-8-pentyl-3-cinnolinecarbonitrile, and the reaction time was reduced from 3 hours to 1 hour prior to pouring the reaction onto ice. A crude product was obtained which was purified by flash chromatography over silica gel. Elution with dichloromethane provided the title compound, 0.35 g (55% yield). Recrystallization from dichloromethane/hexane pro- The procedure of Example 60(a) was used to make more compounds of Formula I, except that the appropriate Grignard reagent* was used instead of butylmagnesium chloride so that R had the correct value as shown in Table VII. Compounds of Formula I listed in Table VII were obtained (R$^3$=COCR$^{10}$R$^{11}$R, R$^4$=NH$_2$, R$^5$=R$^6$=R$^7$=R$^{10}$=R$^{11}$=H, R$^8$=propyl and R as listed in Table VII):

*If not themselves commercially available, the Grignard reagents were generated by reaction of equimolar amounts of magnesium metal turnings with the appropriate alkyl halide in THF for 2 hours. These alkyl halides were commercially available.

TABLE VII

| Example | R | Yield | Melting Point (recryst. solvent) | Formula | Calculated C | H | N | Found C | H | N |
|---|---|---|---|---|---|---|---|---|---|---|
| 61 | ethyl | 86% | 159.5–160.5° (CH$_2$Cl$_2$/hexane) | C$_{15}$H$_{19}$N$_3$O | 70.01 | 7.44 | 16.33 | 69.77 | 7.28 | 16.00 |
| 62 | butyl | 79% | 124.5–125.5° (CH$_2$Cl$_2$/hexane) | C$_{17}$H$_{23}$N$_3$O | 71.55 | 8.12 | 14.72 | 71.22 | 8.02 | 14.50 |
| 63 | 2-propenyl | 32% | 134–136° (CH$_2$Cl$_2$/hexane) | C$_{16}$H$_{19}$N$_3$O | 71.35 | 7.11 | 15.60 | 70.91 | 7.06 | 15.46 |

EXAMPLE 64 a. 4-Amino-8-butyl-N-cyclopropylmethyl-3-cinnolinecarboxamide (Formula I, $R^3$=CONRR$^9$, $R^4$=NH, $R^5$=$R^6$=$R^7$=R=H, $R^8$=butyl, $R^9$=cyclopropylmethyl)

A larger scale preparation of the product of Example 20 is as follows. A suspension of 4-amino-8-butyl-3-cinnolinecarboxylic acid (25.0 g) in dry DMF (625 ml) was prepared by gradual addition of the solid to the rapidly stirred solvent at room temperature under nitrogen. To this suspension was added 1,1'-carbonyldiimidazole (19.96 g), and the mixture was stirred at room temperature a further 60 min. The resulting clear light brown solution was cooled to 0°, and (aminomethyl)cyclopropane (8.71 g) was added by syringe with vigorous stirring. After 2 hours at 0°, the mixture was allowed to come to room temperature. The mixture was diluted with ethyl acetate (500 ml), and water (500 ml) was added. The phases were separated and the organic layer was washed three times with water (500 ml each) and once with brine (500 ml). After drying (Na$_2$SO$_4$), the solution was filtered through a plug of silica gel atop a bed of diatomaceous earth, and the plug was washed with ethyl acetate. The combined filtrate and ethyl acetate wash was evaporated to provide 25.83 g (85% yield) of the title compound as a light tan solid. Analytically pure material was obtained by the following procedure. This 25.83 g of material was combined with 23.11 g of product from another repetition of this method. After dissolution in ethyl acetate (300 ml), the solid was deposited by evaporation onto flash silica gel (100 g). This material was placed atop a column of additional flash silica gel (250 g) in hexane/ethyl acetate (3:1 v/v). Elution with this solvent mixture provided the purified product, 45.93 grams, after evaporation of the appropriate fractions. This material was recrystallized from toluene/hexane to provide 38.53 g of analytically pure white crystals, m.p. 125°–127°. $^1$H NMR (CHCl$_3$-d, characteristic peaks only): 0.30 (m, 2H): 0.56 (m, 2H), 0.96 (t, 3H), 3.34–3.45 (m, 4H), 8.68 (br. s, exchangeable, 1H) ppm.

Calculated for C$_{17}$H$_{22}$N$_4$O: C, 68.43; H, 7.43; N, 18.78. Found: C, 68.41; H, 7.30; N, 18.76.

b. 2-Methyl-3-propylindole

Phenylhydrazine (162.2 g) was placed in a reaction flask fitted with a mechanical stirrer, reflux condenser with attached drying tube, internal thermometer, and addition funnel. Acetic acid (900 ml) was added, resulting in an orange solution. To this mixture was then added 2-hexanone (170 g) over 5 min, and the resulting mixture was heated to reflux with stirring for three hours. After cooling, the acetic acid solvent was removed by rotary evaporation, and the residue was poured into water (4.5 liters). This mixture was extracted three times with ethyl ether (1 liter each) and the combined organic extracts were washed twice with 1N HCl (1 liter each), once with water (1.5 liters), once with saturated sodium bicabonate solution (1 liter) and then once with brine (1 liter). The organic layer was then dried (MgSO$_4$) and evaporated to afford an oil which was purified by two successive vacuum distillations. The title compound (72.1 g) was obtained as an oil distilling between 91.5° and 95° at a pressure of 0.0067 Pascals (0.05 mTorr). An additional portion of the title compound was obtained by chromatography of the stillpot residue over flash silica gel (500 g), eluting with dichloromethane. Evaporation of the appropriate fractions afforded more material which was combined with the distillate above to provide a total of 159.1 grams (61% yield) of the title compound, which was used immediately in step (c).

c. N-[2-(1-Oxobutyl)phenyl]acetamide

A solution of 2-methyl-3-propylindole (159 g) in methanol (1370 ml) was stirred under nitrogen while a solution of sodium periodate (430.4 g) in water (2450 ml) was added over a period of one hour. External cooling was applied as necessary to maintain the reaction temperature at or below 25°. After stirring at room temperature overnight, the mixture was diluted with water (7 liters) and was extracted with dichloromethane (2 liters). The phases were separated, and the aqueous layer was extracted twice more with dichloromethane (1 liter each). The combined organic phases were washed twice with water (1.5 liter each), dried (MgSO$_4$), and evaporated to provide 246.5 grams of crude product. This material was purified by two successive chromatographies over flash silica gel, eluting the desired product with dichloromethane. Upon evaporation of the appropriate fractions, there was obtained 160.6 grams (85% yield) of the title compound as a white crystalline solid, m.p. 46.5°–47°.

d. N-[2-(1-Hydroxybutyl)phenyl]acetamide

A solution of sodium borohydride (30.54 g) in absolute ethanol (2400 ml) was prepared and stirred under nitrogen while cooling to 5°. With external cooling as necessary to maintain the internal temperature between 5° and 7°, a solution of N-[2-(1-oxobutyl)phenyl]acetamide (156 g) in dry THF (1200 ml) was added over a 25 min period. After the addition was complete, the mixture was allowed to warm to room temperature overnight with stirring under nitrogen. The solvents were removed by rotary evaporation, and the residue was treated with water (1575 ml). The resulting mixture was cooled on ice while 1N HCl (945 ml) was added in small portions until gas evolution had ceased. Solid potassium carbonate (150 g) was then added cautiously, and the resulting solution was extracted with ethyl acetate (1575 ml). The organic phase was washed with brine (1 liter), dried (MgSO$_4$), and evaporated to afford 156.1 grams (99% yield) of the title product as a yellow oil. This material was employed in step (e) without further purification.

e. N-(2-Butylphenyl)acetamide

A suspension of 10% (w/w) palladium on carbon (7.8 g, wet with an additional 50% by weight of water) in absolute ethanol (625 ml) containing N-[2-(1-hydroxybutyl)phenyl]acetamide (156 g) was prepared, and concentrated hydrochloric acid (3.2 ml) was added. The mixture was shaken under a positive pressure of about 345,000 Pascals (50 pounds per square inch gauge reading) of hydrogen gas. When hydrogen uptake had ceased (in about 24 hours), the mixture was filtered through diatomaceous earth, and the filtrate was concentrated at reduced pressure to afford 135.3 grams (94% yield) of the title compound as a white solid, m.p. 96.5°–99.5°. This material was used in step (f) without further purification.

f. 2-Butylaniline hydrochloride (Formula XI, $R^5$=$R^6$=$R^7$=H, $R^8$=butyl, hydrochloride salt)

A mixture of N-(2-butylphenyl)acetamide (135.3 g), concentrated hydrochloric acid (300 ml) and 95% ethanol (300 ml) was heated to reflux with stirring for 4 hours. After cooling to room temperature, the mixture was diluted with water (800 ml) and cooled on ice while solid potassium carbonate (about 275 g) was added cautiously to a pH of 10. This solution was extracted twice with ethyl ether (750 ml each) and the combined ether extracts were washed with brine (1 liter) and dried (MgSO$_4$). Evaporation of the solvent provided an oil which was distilled at 0.008 to 0.013 Pascals (0.06 to 0.1 mTorr), providing 100.1 grams of liquid which distilled between 55° and 60°. This distillate was dissolved in ethyl ether (800 ml), and a saturated ethereal solution of hydrogen chloride (400 ml) was added with vigorous stirring under nitrogen. The precipitate which formed was collected by filtration, washed with ethyl ether, and dried in a vacuum dessicator over phosphorus pentoxide to provide 122.8 grams (94% yield) of the title compound as white crystals, m.p. 144.5°-146°.

g. 2-[(2-Butylphenyl)hydrazono]-2-cyanoacetamide (Formula X, $R^5=R^6=R^7=R=H$, $R^8=$butyl)

A suspension of 2-butylaniline hydrochloride (61.89 g) was prepared in a prechilled solvent mixture of acetic acid (200 ml), water (128 ml), and concentrated hydrochloric acid (72 ml) and was held at $-15°$ with efficient stirring. With strong external cooling as necessary to maintain the internal temperature between $-13°$ and $-15°$, a solution of sodium nitrite (25.68 g) in water (117 ml) was added in a dropwise manner over about 20 min. The resulting clear solution was held at $-18°$ for 15 min, and was then filtered into a waiting, prechilled ($-7°$) solution of 2-cyanoacetamide (84.08 g) in water (3.33 liters) containing sodium acetate (444.5 g). There was an immediate color change to deep yellow, followed by formation of a yellow precipitate. The reaction mixture was stirred in a $-12°$ bath for three days. After warming to 0°, the precipitated product was isolated by filtration, and was washed with hexane (300 ml), then ice-cold water (300 ml), and again with hexane (300 ml). After drying in vacuo at 40° over phosphorus pentoxide, the title compound was obtained as a mixture of (E)- and (Z)-isomers in a ratio of about 2:1: 77.39 grams of yellow powder (95% yield), m.p. 160°-162°.

In another preparation, a portion of the title compound was recrystallized from ethyl acetate/hexane, providing an analytical sample in which the (E)-isomer predominated, and which gave m.p. 130°-138°.

Calculated for C$_{13}$H$_{16}$N$_4$O: C, 63.92; H, 6.60; N, 22.93. Found: C, 63.77; H, 6.73; N, 22.84.

h. 4-Amino-8-butyl-3-cinnolinecarboxamide (Formula IX, $R^5=R^6=R^7=H$, $R^8=$butyl)

Three identical reaction mixtures were prepared as follows: A suspension of 2-[(2-butylphenyl)hydrazono]-2-cyanoacetamide (25.59 g) in dry toluene (600 ml) was stirred under nitrogen while anhydrous aluminum chloride (35 g) was added. The mixtures were heated to 90° with stirring under nitrogen for 3.5 hours. After cooling to room temperature, each was diluted with ethyl acetate (800 ml). With external cooling and efficient stirring, 20% (w/v) sodium hydroxide solution was added in a dropwise manner until the deep orange color of each mixture was fully discharged. To each mixture was then added an additional portion of 20% (w/v) sodium hydroxide solution (500 ml), and the resulting suspensions were stirred with cooling on ice for 2 hours. The phases were then separated, and the aqueous layers were discarded. The organic layers containing the suspended product were then washed with 20% (w/v) sodium hydroxide (250 ml each), and these aqueous layers were also discarded. Finally, the organic phases were washed with water (250 ml each). The suspended product was then isolated by filtration of the combined organic phases. This solid was washed with water (300 ml), twice with ethyl acetate (300 ml each), and twice with ethyl ether (300 ml each). After drying in vacuo at 45° over phosphorus pentoxide, there was obtained 73.50 grams (96% yield) of the title compound as a white solid.

Using material from another repetition of this preparation, a portion of the title compound was recrystallized from ethanol, providing an analytical sample, m.p. 215°-217.5°.

Calculated for C$_{13}$H$_{16}$N$_4$O: C, 63.92; H, 6.60; N, 22.93. Found: C, 63.61; H, 6.48; N, 22.45.

i. 4-Amino-8-butyl-3-cinnolinecarboxylic acid (Formula VI, $R^5=R^6=R^7=H$; $R^8=$butyl, A$=$COOH)

Two identical reaction mixtures were prepared as follows: A mixture of 4-amino-8-butyl-3-cinnolinecarboxamide (36.71 g), absolute ethanol (1400 ml), and 20% (w/v) aqueous sodium hydroxide solution (300 ml) was brought to reflux with stirring for 6 hours. After cooling to room temperature, the ethanol solvent of each mixture was removed by rotary evaporation. The solid residues were combined and treated with water (2.5 liters). Using efficient stirring and external cooling, concentrated hydrochloric acid was added to achieve a final pH of 5.1. After cooling to 0°, the precipitated solid was collected by filtration, and was washed twice with water (250 ml each) and twice with ethyl ether (250 ml each). After drying in vacuo at 45° over phosphorus pentoxide, there was obtained 62.77 grams (85% yield) of the title compound as a slightly yellowish-white powder.

Using material from another repetition of this preparation, a portion of the title compound was recrystallized from ethanol, providing an analytical sample, m.p. 218°-220°.

Calculated for C$_{13}$H$_{15}$N$_3$O$_2$: C, 63.65; H, 6.16; N, 17.13. Found: C, 63.23; H, 6.14; N, 16.70.

EXAMPLE 65

4-Amino-8-butyl-N-cyclopropylmethyl-3-cinnolinecarboxamide hydrochloride monohydrate (Formula I, $R^3=$CONRR$^9$, $R^4=$NH$_2$, $R^5=R^6=R^7=R=H$, $R^8=$butyl, $R^9=$cyclopropylmethyl, hydrochloride salt monohydrate)

To a rapidly stirred solution of a portion of the product of Example 64 (6.0 g) in ethyl ether (650 ml) was added an ethereal solution of hydrogen chloride until no further precipitate formed. The mixture was cooled to 0° and then filtered. After washing the collected solid with two portions of ethyl ether (50 ml each), the product was dried at 35° in vacuo. There was thus obtained 6.73 grams (95.6% yield) of the title compound as a slightly yellowish white solid, m.p. 174°-181.5° (with decomposition).

Calculated for C$_{17}$H$_{22}$N$_4$O.HCl.H$_2$O: C, 57.86; H, 7.14; N, 15.88. Found: C, 57.60; H, 6.93; N, 15.48.

EXAMPLE 66 a. 4-Amino-N-cyclopropylmethyl-8-propyl-3-cinnolinecarboxamide (Formula I, $R^3=$CONRR$^9$, $R^4=$NH$_2$, $R^5=R^6=R^7=R=H$, $R^8=$propyl, $R^9=$cyclopropylmethyl)

A larger scale preparation of the product of Example 26 is as follows. A suspension of 4-amino-8-propyl-3-cinnolinecarboxylic acid (39.8 g) was prepared in dry DMF (1 liter) by slow addition of the solid to the vigorously stirred solvent under an atmosphere of nitrogen. To this suspension was added 1,1'-carbonyldiimidazole (40 g) in small portions over a period of 1 hour with vigorous stirring. After an additional hour, triethylamine (29 g, dried by distillation from potassium hydroxide) was added, followed by (aminomethyl)cyclopropane hydrochloride (23 g). The resulting mixture was stirred for 1.5 hours at room temperature under nitrogen. It was then poured into water (1300 ml) and the product was extracted into five portions of ethyl acetate (500 ml each). The combined organic layers were washed with brine (1 liter), dried (MgSO4), and evaporated to afford a light brown solid. This material was purified by chromatography over silica gel according to the following procedure. After dissolution in ethyl acetate (1 liter), the crude product was evaporated onto flash silica gel (250 g). This was loaded atop a column of additional flash silica gel (1 kg) in hexanes/ethyl acetate (3:1 v/v). The desired product was eluted from the column with hexanes/ethyl acetate (2:1 v/v). Appropriate fractions were combined and evaporated to provide 39.01 grams (80% yield) of the title compound as a white solid. Recrystallization from toluene/hexane provided 31.5 grams of analytically pure material as white crystals, m.p. 128°–129°. $^1$H NMR (CHCl$_3$-d, characteristic peaks only): 0.30 (m, 2H), 0.57 (m, 2H), 1.05 (t, 3H), 3.35–3.42 (m, 4H), 8.69 (br. s, exchangeable, 1H) ppm.

Calculated for $C_{16}H_{20}N_4O$: C, 67.58; H, 7.09; N, 19.70. Found: C, 67.52; H, 7.09; N, 19.68.

b. 2-Cyano-2-[(2-propylphenyl)hydrazono]acelamide (Formula X, $R^5 = R^6 = R^7 = H$, $R^8 = $ propyl)

The hydrochloride salt of 2-propylaniline was prepared by dissolution of a commercial sample of 2-propylaniline in ethyl ether and addition of an ethereal solution of hydrogen chloride until no further precipitate formed. This precipitate was collected by filtration, washed with ether, and dried briefly in vacuo to provide 2-propylaniline hydrochloride, which was used immediately according to the following procedure. A suspension of this material (34.33 g) was prepared in a prechilled solvent mixture of acetic acid (120 ml), water (77 ml), and concentrated hydrochloric acid (43.4 ml), and was held at −12° with efficient stirring. Using strong external cooling as necessary to maintain an internal temperature between −15° and −10°, a solution of sodium nitrite (14.21 g) in water (67 ml) was added over a period of about 20 min. The mixture was then stirred at −18° for 15 min, and was then filtered into a waiting, prechilled (−7°) solution of 2-cyanoacetamide (50.44 g) in water (2.0 liters) containing sodium acetate (266.7 g). There was an immediate color change to deep yellow followed by the formation of a yellow precipitate. The reaction mixture was stirred in a −11° bath for two days. After warming to 10°, the precipitate was collected by filtration, and was washed alternately with hexanes and ice-cold water. After drying at 45° in vacuo over phosphorus pentoxide, there was obtained 42.12 grams (91% yield) of the title compound as a mixture of (E)- and (Z)-isomers.

Using material from a repetition of this method, a portion of the title compound was recrystallized from ethyl acetate/hexane, providing an analytical sample of the (E)-isomer, m.p. 128°–130°.

Calculated for $C_{12}H_{14}N_4O$: C, 62.59; H, 6.13; N, 24.33. Found: C, 62.56; H, 6.16; N, 24.37.

c. 4-Amino-8-propyl-3-cinnolinecarboxamide (Formula IX, $R^5 = R^6 = R^7 = H$, $R^8 = $ propyl)

Two identical reaction mixtures were prepared as follows: a suspension of 2-[(2-butylphenyl)hydrazono]-2-cyanoacetamide (21.05 g) in dry toluene (502 ml) was stirred under nitrogen while anhydrous aluminum chloride (30.5 g) was added. These mixtures were heated to 90° with stirring for two hours. After cooling to room temperature, each was diluted with ethyl acetate (800 ml). Using external cooling and efficient stirring, 20% (w/v) sodium hydroxide solution was added in a dropwise fashion until the orange color of each reaction mixture was fully discharged. When these additions were complete, a further portion of 20% (w/v) sodium hydroxide solution (500 ml) was added to each mixture, and the resulting suspensions were stirred with external ice cooling for 2 hours. The phases were then separated, and the aqueous layers were discarded. The organic phases, containing the suspended product, were gently shaken with 20% (w/v) sodium hydroxide solution (250 ml) and these aqueous layers were also discarded. Finally, each organic phase was washed with water (250 ml). At this point the suspended solid product was isolated by filtration of the combined organic layers. After washing with water (250 ml), twice with ethyl acetate (200 ml each), and three times with ethyl ether (200 ml each), the resulting solid was dried in vacuo at 45° over phosphorus pentoxide. There was thus obtained 40.17 grams (95% yield) of the title compound as a white solid.

Using material from a repetition of this method, a portion of the title compound was recrystallized from ethanol, providing an analytical sample, m.p. 249°–250°.

Calculated for $C_{12}H_{14}N_4O$: C, 62.59; H, 6.13; N, 24.33. Found: C, 62.31; H, 6.30; N, 23.47.

d. 4-Amino-8-propyl-3-cinnolinecarboxylic acid (Formula VI, $R^5 = R^6 = R^7 = H$, $R^8 = $ propyl, A=COOH)

A suspension of 4-amino-8-propyl-3-cinnolinecarboxamide (40.1 g) in ethanol (1650 ml) was treated with 20% (w/v) aqueous sodium hydroxide solution (348 ml), and the mixture was heated to reflux under nitrogen for eight hours. After cooling to room temperature, the ethanol solvent was removed by rotary evaporation, and the residue was suspended in water (1500 ml). Using external cooling as necessary to maintain the internal temperature below 40°, concentrated hydrochloric acid was added with efficient stirring until a final pH of 5.0 was reached. After cooling to 0°, the precipitated product was isolated by filtration, and was washed twice with ice-cold water (200 ml each) and four times with ethyl ether (200 ml each). After drying in vacuo at 45° over phosphorus pentoxide, the title compound (39.50 g, 98% yield) was obtained as a white solid.

Using material from a repetition of this method, a portion of the title compound was recrystallized from ethanol, providing an analytical sample, m.p. 224° (with decomposition).

Calculated for $C_{12}H_{13}N_3O_2$: C, 62.33; H, 5.67; N, 18.17. Found: c, 61.99; H, 5.85; N, 17.89.

EXAMPLE 67

4-Amino-N-cyclopropylmethyl-8-propyl-3-cinnolinecarboxamide hydrochloride monohydrate (Formula I, $R^3 = CONRR^9$, $R^4 = NH_2$, $R^5 = R^6 = R^7 = R = H$, $R^8 = $ propyl, $R^9 = $ cyclopropylmethyl, hydrochloride salt monohydrate)

To a rapidly stirred solution of a portion of the product of Example 66 (6.5 g) in ethyl ether (750 ml) was added a solution of hydrogen chloride in ethyl ether until no further precipitate formed. The mixture was stirred at room temperature for 15 min, and then filtered. The collected solid was washed with ethyl ether (approximately 150 ml) and then with hexane (approximately 150 ml), and finally dried at room temperature in vacuo. There was thus obtained 7.2 grams (98% yield) of the title compound as a slightly yellowish-white solid, m.p. 212°–218° (with decomposition).

Calculated for $C_{16}H_{20}N_4O\cdot HCl\cdot H_2O$: C, 56.73; H, 6.84; N, 16.54. Found: C, 56,96; H, 6.69; N, 16.32.

EXAMPLE 68

8-Chloro-4-hydroxy-N-propyl-3-cinnolinecarboxamide (Formula I, $R^3$=CONRR$^9$, $R^4$=OH, $R^5$=$R^6$=$R^7$=R=H, $R^8$=chloro, $R^9$=propyl)

To a suspension of a portion of the product of Example 33(a) (0.98 g) in absolute ethanol (25 ml) was added solid potassium hydroxide (3.0 g). The mixture was stirred and heated to reflux under nitrogen for 48 hours. The mixture was poured into water (100 ml) and the resulting suspension was extracted twice with ethyl ether (100 ml each); these ether extracts were discarded. The residual aqueous suspension was acidified to a final pH of 5.5 (to test papers) by the dropwise addition of glacial acetic acid with stirring. After chilling to 0° with stirring for three hours, the precipitated product was collected by filtration, washed with water, and dried in vacuo at 40° over phosphorus pentoxide. This provided 0.80 grams (80% yield) of the title compound as a white solid. Recrystallization from boiling methanol provided an analytical sample of white felt-like fine needles, m.p. 237°–239°. $^1$H NMR (DMSO-d$_6$, characteristic peaks only): 3.31(t, 2H), 7.55(t,d of d,1H), 8.05(d of d,1H), 8.16(d of d,1H), 9.45(t, exchangeable, 1H), 14.12(s, exchangeable, 1H) ppm.

Calculated for $C_{12}H_{12}N_3O_2Cl$: C, 54.25; H, 4.55; N. 15.81. Found C, 53.93, H, 4.44; N, 15.60.

EXAMPLE 69

1-(4-Amino-8-propylcinnolin-3-yl)-1-propanone (Formula I, $R^3$=COCR$^{10}$R$^{11}$, $R^4$=NH$_2$, $R^5$=$R^6$=$R^7$=$R^{10}$=$R^{11}$=H, $R^8$=propyl, R=ethyl)

The procedure of Example 60(a) was used except that ethylmagnesium iodide was substituted for butylmagnesium chloride. A crude product was obtained which was purified by flash chromatography over silica gel. Elution with dichloromethane provided the title compound, 0.76 g (87% yield). Recrystallization from dichloromethane/hexane provided an analytical sample of white crystals, m.p. 187°–188°. $^1$H NMR (DMSO-d$_6$, characteristic peaks only): 0.98 (t, 3H), 1.19 (t, 3H), 3.31 (t, 2H), 3.41 (q, 2H) ppm.

Calculated for $C_{14}H_{17}N_3O$: C, 69.11; H, 7.04; N, 17.27. Found: C, 68.85; H, 7.09; N, 17.36.

EXAMPLE 70

4-Amino-8-butyl-N-cyclobutylmethyl-3-cinnolinecarboxamide (formula I, $R^3$=CONRR$^9$, $R^4$=NH$_2$, $R^5$=$R^6$=$R^7$=R=H, $R^8$=butyl, $R^9$=cyclobutylmethyl)

Following the procedures of Examples 17(a)–(d) but substituting (aminomethyl)cyclobutane for the 2-propenylamine used in Example 17(a), the title compound was obtained in 62% yield as a beige solid. Recrystallization from toluene/hexane provided an analytical sample of white crystals, m.p. 118.5°–119.5°. $^1$H NMR (CHCl$_3$-d, characteristic peaks only): 0.96 (t, 3H), 3.41 (t, 2H), 3.54 (t, 3H), 8.55 (br. s, exchangeable, 1H) ppm.

Calculated for $C_{18}H_{24}N_4O$: C, 69.20; H, 7.74; N, 17.93. Found: C, 69.27; H, 7.74; N, 17.84.

(Aminomethyl)cyclobutane was prepared by lithium aluminum hydride reduction of cyclobutanecarboxamide according to the procedure of Shatkina, T. N.: Reutov, O. A., *Dokl. Akad. Nauk. SSSR.* (1975) 219:1148 [*Chem. Abs.* 82: 139453m]. Cyclobutanecarboxamide was prepared as follows: a solution of commercially available cyclobutanecarboxylic acid chloride (10 g) in ethyl ether (500 ml) was stirred at 0° while ammonia gas was introduced, resulting in a white precipitate. This material was collected by filtration and redissolved in 50 ml of ethanol/water (4:1, v/v). This solution was applied to a column containing 75 grams of AG 1-X8 ion exchange resin (hydroxide ion form) (obtained from Bio-Rad Company), and elution was continued with ethanol (1 liter). Evaporation of the eluate provided a quantitative yield (8.36 g) of cyclobutanecarboxamide.

EXAMPLE 71

1-[(4-Amino-8-butyl-3-cinnolinyl)carbonyl]-2,5-dihydro-1H-pyrrole (Formula I, $R^3$=CONRR$^9$, $R^4$=NH$_2$, $R^5$=$R^6$=$R^7$=H, $R^8$=butyl, R and $R^9$, taken together, are —CH$_2$CH=CHCH$_2$—)

Following the procedures of Examples 17(a)–(d), but substituting a commercial sample of pyrroline (75% purity, obtained from Aldrich) for the 2-propenylamine used in Example 17(a), the title compound was obtained as a light yellowish-orange tinted powder in 20% yield after recrystallization from ethyl acetate, m.p. 164°–165° (with decomposition). Attempts to purify this material by further recrystallization led to extensive decomposition. $^1$H NMR (CHCl$_3$-d, characteristic peaks only): 0.96 (t, 3H), 4.58 (m, 2H), 5.00 (m, 2H), 5.90 (br. s, 2H) ppm.

Calculated for $C_{17}H_{20}N_4O$: C, 68.90; H, 6.80; N, 18.90. Found: C, 67.96; H, 6.67; N, 18.58.

EXAMPLE 72

4-Amino-8-butyl-N-cyclopropyl-3-cinnolinecarboxamide hydrochloride ¼ hydrate (Formula I, $R^3$=CONRR$^9$, $R^4$=NH$_2$, $R^5$=$R^6$=$R^7$=R=H, $R^8$=butyl, $R^9$=cyclopropyl, hydrochloride salt ¼ hydrate)

Following the procedures of Examples 17(a)–(d), but substituting cyclopropylamine for the 2-propenylamine used in Example 17(a), the free base form of the title compound was obtained as a white solid in 86% yield. This material was dissolved in ethyl ether, filtered, and a solution of hydrogen chloride in ether was added to the filtrate until no further precipitate formed. This material was collected by filtration and dried in vacuo, providing the title compound in 55% yield, m.p. 198°–210° (with decomposition). $^1$H NMR (DMSO-d$_6$, characteristic peaks only): 0.69–0.79 (m, 4H), 0.91 (t, 3H), 2.95 (m, 1H), 3.20 (t, 3H) ppm.

Calculated for $C_{16}H_{20}N_4O\cdot HCl\cdot$¼ $H_2O$: C, 59.07; H, 6.66; N, 17.22. Found: C, 58.93; H, 6.84; N, 17.18.

EXAMPLE 73

4-Amino-N-methyl-8-propyl-N-(2-propynyl)-3-cinnolinecarboxamide (Formula I, $R^3$=CONRR$^9$, $R^4$=NH$_2$, $R^5$=$R^6$=$R^7$=H, $R^8$=propyl, $R^9$=2-propynyl, R=methyl)

Following the procedures given in Examples 23(a)–(d), but replacing the 2-propenylamine used in Example 23(a) with N-methyl-N-(2-propynyl)amine, the title compound was obtained as a light brown solid in 38% yield after recrystallization from toluene, m.p. 133°–135° (with decomposition). Attempted purification by further recrystallization led to extensive decomposition. $^1$H NMR (CHCl$_3$-d, characteristic peaks only): 1.04 (t, 3H), 2.28 (br. s, 1H), 4.46 and 4.83 (two br. singlets, 2H) ppm.

Calculated for C$_{16}$H$_{18}$N$_4$O: C, 68.09; H, 6.43; N, 19.84. Found: C, 68.43; H, 6.48; N, 19.03.

EXAMPLE 74

4-Amino-N-(2-methylpropyl)-8-propyl-3-cinnolinecarboxamide (Formula I, R$^3$=CONRR$^9$, R$^4$=NH$_2$, R$^5$=R$^6$=R$^7$=R=H, R$^8$=propyl, R$^9$=2-methylpropyl)

Following the procedures given in Examples 23(a)-(d), but replacing the 2-propenylamine used in Example 23(a) with 2-methylpropylamine, the title compound was obtained as off-white crystals in 46% yield after recrystallization from toluene/hexane, m.p. 104°-110°. $^1$H NMR (CHCl$_3$-d, characteristic peaks only): 1.02 (d, 6H), 1.05 (t, 3H), 3.30-3.42 (m, 2H), 8.50 (br. t, exchangeable, 1H) ppm.

Calculated for C$_{16}$H$_{22}$N$_4$O: C, 67.11; H, 7.74; N, 19.56. Found: C, 66.91, H, 7.63; N, 19.63.

EXAMPLE 75

1-[(4-Amino-8-propyl-3-cinnolinyl)carbonyl]pyrrolidine (Formula I, R$^3$=CONRR$^9$, R$^4$=NH$_2$, R$^5$=R$^6$32 R$^7$=H, R$^8$=propyl, R and R$^9$, taken together, are —CH$_2$CH$_2$CH$_2$CH$_2$—)

Following the procedures given in Examples 23(a)-(d), but replacing the 2-propenylamine used in Example 23(a) with pyrrolidine, the title compound was obtained as white crystals in 67% yield after recrystallization from toluene/hexane, m.p. 154°-156°. $^1$H NMR (CHCl$_3$-d, characteristic peaks only): 1.04 (t, 3H), 3.42 (t, 3H), 3.77 (t, 2H), 4.11 (t, 2H) ppm.

Calculated for C$_{16}$H$_{20}$N$_4$O: C, 67.58; H, 7.09; N, 19.70. Found: C, 67.38; H, 7.11; N, 19.56.

gen chloride was added until no further precipitate formed. This material was collected and dried in vacuo to provide the title compound as a white powder in 78% yield, m.p. 142°-150°. $^1$H NMR (DMSO-d$_6$, characteristic peaks only): 0.99 (t, 3H), 1.4-1.8 (m, 6H), 3.13(t, 2H), 3.42 (br. (br. s, 2H) ppm.

Calculated for C$_{17}$H$_{22}$N$_4$O.HCl. ¼H$_2$O: C, 60.17; H, 6.98; N, 16.51. Found: C, 59.88; H, 6.89; N, 16.44.

EXAMPLE 77

4-[(4-Amino-8-propyl-3-cinnolinyl)carbonyl]morpholinehydrochloride 1/6 hydrate (Formula I, R$^3$=CONRR$^9$, R$^4$=NH$_2$, R$^5$=R$^6$=R$^7$=H, R$^8$=propyl, R and R$^9$, taken together, are —CH$_2$CH$_2$—O—CH$_2$CH$_2$—, hydrochloride salt 1/6 hydrate)

Following the procedures given in Examples 23(a)-(d), but replacing the 2-propenylamine used in Example 23(a) with morpholine, the free base form of the title compound was obtained as a clear oil. This was dissolved in ethyl ether and an ethereal solution of hydrogen chloride was added until no further precipitate formed. This material was collected by filtration and dried in vacuo to provide the title compound as a white powder in 55% yield, m.p. 210°-213°. $^1$H NMR (DMSO-d$_6$, characteristic peaks only): 0.99 (t, 3H), 3.13 (t, 2H), 3.55 (m, 4H), 3.76 (br. s, 4H) ppm.

Calculated for C$_{16}$H$_{20}$N$_4$O$_2$.HCl.C, 56.65; H, 5.98; N, 16.49. Found: C, 56.54; H, 6.23; N, 16.07.

EXAMPLES 78(a)-80(a)

Following the procedure of Example 33(a) for reaction of the appropriate 2-cyano-N-propyl-2-[(substituted-phenyl)hydrazono]acetamide with aluminum chloride, compounds of Formula I (R$^3$=CONRR$^9$, R$^4$=NH$_2$, R=H, R$^9$=propyl, and R$^5$, R$^6$, R$^7$, and R$^8$ as listed in Table VIII) were prepared as listed in Table VIII.

TABLE VIII

| Example | R$^5$ | R$^6$ | R$^7$ | R$^8$ | Yield | Melting point (recryst. solvent) | Formula | Calculated | | | Found | | |
|---------|-------|-------|-------|-------|-------|----------------------------------|---------|------------|---|---|-------|---|---|
| | | | | | | | | C | H | N | C | H | N |
| 78(a)* | H | Cl | H | Cl | 28% | 228-228.5° (ethyl acetate) | C$_{12}$H$_{12}$N$_4$OCl$_2$ | 48.18 | 4.04 | 18.73 | 48.30 | 4.25 | 18.66 |
| 79(a)* | Cl | H | H | Cl | 42% | 134.0-134.5° (ethyl acetate/hexane) | C$_{12}$H$_{12}$N$_4$OCl$_2$ | 48.18 | 4.04 | 18.73 | 48.22 | 4.08 | 18.76 |
| 80(a) | H | H | Cl | CH$_3$ | 83% | 231-231.5° (ethyl acetate) | C$_{13}$H$_{15}$N$_4$OCl | 56.02 | 5.42 | 20.10 | 56.06 | 5.37 | 19.86 |

*Notes:
Example 78(a): reaction temperature increased to the boiling point of the solvent; reaction time increased to 8 hours.
Example 79(a): reaction temperature increased to the boiling point of the solvent; reaction time increased to 28¼ hours.

EXAMPLE 76

1-[(4-Amino-8-propyl-3-cinnolinyl)carbonyl]piperidine hydrochloride ¼ hydrate (Formula I, R$^3$=CONRR$^9$, R$^4$=NH$_2$, R$^5$=R$^6$=R$^7$=H, R$^8$=propyl, R and R$^9$, taken together, are —CH$_2$CH$_2$CH$_2$CH$_2$CH$_2$—, hydrochloride salt ¼hydrate)

Following the procedures given in Examples 23(a)-(d), but replacing the 2-propenylamine used in Example 23(a) with piperidine, the free base form of the title compound was obtained as a clear oil. This was dissolved in ethyl ether and an ethereal solution of hydro-

EXAMPLES 78(b)-80(b)

To obtain the required starting materials for Examples 78(a)-80(a), the procedure of Example 33(b) was employed, substituting the appropriate aniline for 2-chloroaniline. The 2-cyano-N-propyl-2-[(substituted-phenyl)hydrazono]acetamides, compounds of Formula VIII where R=H, R$^9$=propyl, and R$^5$, R$^6$, R$^7$ and R$^8$ as listed in Table IX, were obtained as mixtures of (E)- and (Z)-isomers. These compounds are listed in Table IX.

TABLE IX

| Example | R⁵ | R⁶ | R⁷ | R⁸ | Yield | Melting point (recryst. solvent) | Formula | Calculated C | H | N | Found C | H | N |
| --- | --- | --- | --- | --- | --- | --- | --- | --- | --- | --- | --- | --- | --- |
| 78(b) | H | Cl | H | Cl | 81% | 197–199° (ethyl acetate/hexane) | $C_{12}H_{12}N_4OCl_2$ | 48.18 | 4.04 | 18.73 | 48.23 | 4.10 | 18.60 |
| 79(b) | Cl | H | H | Cl | 92% | 177–178° (ethyl acetate/hexane) | $C_{12}H_{12}N_4OCl_2$ | 48.18 | 4.04 | 18.73 | 48.20 | 4.16 | 18.71 |
| 80(b) | H | H | Cl | CH₃ | 97% | 148–149° (ethyl acetate/hexane) | $C_{13}H_{15}N_4OCl$ | 56.02 | 5.42 | 20.10 | 55.88 | 5.57 | 20.23 |

EXAMPLE 81 a. 4-Amino-8-butyl-7-chloro-N-propyl-3-cinnolinecarboxamide (Formula I, $R^3$=CONRR⁹, $R^4$=NH₂, $R^5$=$R^6$=R=H, $R^7$=chloro, $R^8$=butyl, $R^9$=propyl)

To a suspension of 4-amino-8-butyl-7-chloro-3-cinnolinecarboxylic acid (1.2 g) in dry DMF (30 ml) was added 1,1'-carbonyldiimidazole (0.84 g) and the mixture was stirred at room temperature under nitrogen for two hours. Propylamine (0.425 ml) was then added, and the mixture was stirred at room temperature for an additional 30 min. Ethyl acetate (75 ml) was then added, and the mixture was washed three times with water (100 ml each) and once with brine (100 ml). After drying (MgSO₄) and evaporation of the solvent, the resulting crude product was purified by flash chromatography over silica gel, eluting with hexane/ethyl acetate (2:1, v/v). Appropriate fractions were pooled and evaporated to afford a light beige solid which was recrystallized from ethyl ether/hexane to provide the title compound (0.50 g, 36% yield) as white crystals, m.p. 156°–158°. ¹H NMR (CHCl₃-d, characteristic peaks only): 0.97 (t, 3H), 1.03 (t, 3H), 7.63 (AB quartet, 2H) ppm.

Calculated for $C_{16}H_{21}N_4OCl$: C, 59.90; H, 6.60; N, 17.46. Found: C, 59.90; H, 6.62; N, 17.36.

b. 3-Chloro-N-(2,2-dimethylpropionyl)-2-methylaniline

A commercial sample of 3-chloro-2-methylaniline was purified by redistillation before use. To a solution of this redistilled material (16.5 ml) in dichloromethane (200 ml) was added a saturated aqueous solution of sodium carbonate (200 ml) and the resulting two-phase system was stirred vigorously. Using external cooling as necessary to maintain the internal temperature below 20°, trimethylacetyl chloride (18.71 ml) was added in a dropwise manner. The mixture was stirred at room temperature overnight, and the phases were then separated. The aqueous layer was extracted with an additional 100 ml of dichloromethane. The combined dichloromethane extracts were washed with brine (100 ml), dried (MgSO₄), and evaporated to afford a white solid which was recrystallized from hexane. There was thus obtained 28.79 grams (92% yield) of the title compound as white needles, m.p. 113°–113.5°.

Calculated for $C_{12}H_{16}NOCl$: C, 63.86; H, 7.14; N, 6.20. Found: C, 64.02; H, 7.08; N, 6.36.

c. 2-Butyl-3-chloro-N-(2,2-dimethylpropionyl)aniline

A solution of 3-chloro-N-(2,2-dimethylpropionyl)-2-methylaniline (9.79 g) in dry THF (150 ml) was stirred under nitrogen at 0° while a solution of n-butyllithium in hexane was added in a dropwise fashion until a slight orange color was noted. The volume of n-butyllithium solution which had been added was noted, and an equal volume of this n-butyllithium solution was then added in order to complete formation of the dianion of the starting material. The final deep orange solution was then stirred at 0° for 15 min before adding iodopropane (7.92 g). After 15 min, the reaction mixture was cautiously diluted with water (250 ml) and was extracted with ethyl ether (300 ml). The organic layer was washed with brine, dried (MgSO₄), and evaporated to afford the title compound as a white solid, 11.38 g (97% yield). Recrystallization from hexane provided an analytical sample, m.p. 88°–89°.

Calculated for $C_{15}H_{22}NOCl$: C, 67.28; H, 8.28; N, 5.23. Found: C, 67.43; H, 8.42; N, 4.98.

d. 2-Butyl-3-chloroaniline hydrochloride (Formula XI, $R^5$=$R^6$=H, $R^7$=chloro, $R^8$=butyl)

2-Butyl-3-chloro-N-(2,2-dimethylpropionyl)-aniline (12.89 g) was combined with 6 N hydrochloric acid (145 ml) and HOAc (145 ml) and heated to 90° overnight with stirring. The reaction mixture was then cooled to room temperature, resulting in a white precipitate of the title compound which was filtered out and washed with ethyl ether. The filtrate was made basic by the addition of 20% (w/v) sodium hydroxide solution, and was then extracted with ethyl ether. This organic extract was washed with water and brine in succession, and was then dried (MgSO₄). After chilling to 0°, an ethereal solution of hydrogen chloride was added, resulting in precipitation of another portion of the title compound. This was collected by filtration and combined with the solid isolated earlier to provide a total of 8.47 grams (75% yield) of the title compound, m.p. 169°–179°.

Calculated for $C_{10}H_{14}NCl \cdot HCl$: C, 54.56; H, 6.87; N, 6.36. Found: C, 54.48; H, 6.90; N, 6.17.

e. 2-[(2-Butyl-3-chlorophenyl)hydrazono]-2-cyanoacetamide (Formula X, $R^5$=$R^6$=H, $R^7$=chloro, $R^8$=butyl)

A suspension of 2-butyl-3-chloroaniline hydrochloride (10.37 g) in a mixture of acetic acid (29 ml), concentrated hydrochloric acid (15 ml), and water (45 ml) was chilled to −15° with stirring. To this mixture was added a solution of sodium nitrite (3.41 g) in water (15 ml) in a dropwise manner, maintaining the internal temperature below 0°. The resulting deep yellow solution was stirred at −10° for 15 min, and was then poured all at once into a waiting solution of 2-cyanoacetamide (11.9 g) in water (500 ml) containing sodium acetate (59 g), previously chilled to −10°. The mixture was stirred at 0° for four hours, and was allowed to come to room temperature overnight. The mixture was then diluted with water and the product was extracted into ethyl acetate. The ethyl acetate solution was washed with brine and concentrated to a small volume to produce crystals of the title compound as a mixture of (E)- and (Z)-isomers, 10.90 grams (83% yield), m.p. 164°–166.5°.

Calculated for $C_{13}H_{15}N_4OCl$: C, 56.02; H, 5.42; N, 20.10. Found: C, 55.38; H, 5.35; N, 19.94.

f. 4-Amino-8-butyl-7-chloro-3-cinnolinecarboxamide (Formula IX, $R^5=R^6=H$, $R^7=$chloro, $R^8=$butyl)

To a suspension of 2-[(2-butyl-3-chlorophenyl)hydrazono]-2-cyanoacetamide (10.9 g) in dry toluene (250 ml) was added anhydrous aluminum chloride (13.0 g) and the mixture was heated to 80° with stirring under nitrogen for three hours. After cooling to room temperature, the mixture was diluted with ethyl acetate (500 ml) and cooled to 0°. A 20% (w/v) aqueous solution of sodium hydroxide (300 ml) was then added and the mixture was stirred at or below room temperature for about one hour. The phases were separated, and the organic layer was washed with 20% (w/v) sodium hydroxide solution, water, and brine in succession. Evaporation provided a yellow solid which was triturated with hexane and filtered. Recrystallization of the solid from ethyl acetate provided 5.3 grams (49% yield) of the title compound as a white solid. An analytical sample was prepared by a further recrystallization from ethanol, m.p. 234°–235°.

Calculated for $C_{13}H_{15}N_4OCl$: C, 56.02; H, 5.42; N, 20.10. Found: C, 56.15; H, 5.48; N, 20.07.

g. 4-Amino-8-butyl-7-chloro-3-cinnolinecarboxylic acid (Formula VI, $R^5=R^6=H$, $R^7=$chloro, $R^8=$butyl, A=COOH)

A mixture of 4-amino-8-butyl-7-chloro-3-cinnolinecarboxamide (5.3 g), ethanol (180 ml), and a 20% (w/v) aqueous solution of sodium hydroxide (40 ml) was brought to reflux under nitrogen for 5 hours. The mixture was cooled to room temperature and most of the ethanol was removed by rotary evaporation. The remaining residue was treated with water (200 ml) and was cooled on ice with vigorous stirring while concentrated hydrochloric acid was added to obtain a final pH of 5. The resulting solid was collected by filtration, washed with water, and dried in vacuo over phosphorus pentoxide to provide 2.9 grams (55% yield) of the title compound as a yellowish white solid, m.p. 200°–204°.

EXAMPLE 82

4-Amino-8-butyl-7-chloro-N-cyclopropylmethyl-3-cinnolinecarboxamide (Formula I, $R^3=CONRR^9$, $R^4=NH_2$, $R^5=R^6=R=H$, $R^7=$chloro, $R^8=$butyl, $R^9=$cyclopropylmethyl)

Following the procedure of Example 81(a), but substituting (aminomethyl)cyclopropane for the propylamine, the title compound was obtained in 42% yield after recrystallization from ethyl ether/hexane, m.p. 160.5°–162.5°. $^1$H NMR (CHCl$_3$-d, characteristic peaks only): 0.30 (m, 2H), 0.59 (m, 2H), 0.98 (t, 3H), 7.63 (br. s, 2H) ppm.

Calculated for $C_{17}H_{21}N_4OCl$: C, 61.35; H, 6.36; N, 16.83. Found: C, 61.50; H, 6.41; N, 16.87.

EXAMPLE 83 a. 4-Amino-7-chloro-N,8-dipropyl-3-cinnolinecarboxamide (Formula I, $R^3=CONRR^9$, $R^4=NH_2$, $R^5=R^6=R=H$, $R^7=$chloro, $T^8=^9=$propyl)

Following the procedure of Example 81(a), but substituting 4-amino-7-chloro-8-propyl-3-cinnolinecarboxylic acid for the 4-amino-8-butyl-7-chloro-3-cinnolinecarboxylic acid, the title compound was obtained in 75% yield as an off-white solid. Recrystallization from toluene provided an analytical sample of white crystals, m.p. 167.5°–168.5°. $^1$H NMR (CHCl$_3$-d, characteristic peaks only): 1.03 (t, 3H), 1.10 (t, 3H), 7.63 (br. s, 2H) ppm.

Calculated for $C_{15}H_{19}N_4OCl$: C, 58.73; H, 6.24; N, 18.26. Found: C, 58.88; H, 6.26; N, 18.31.

b. 3-Chloro-N-(2,2-dimethylpropionyl)-2-propylaniline

Following the procedure of Example 81(c), but substituting iodoethane for iodopropane, the title compound was obtained in 73% yield. This material was suitable for the ensuing step without further purification.

c. 3-Chloro-2-propylaniline hydrochloride (Formula XI, $R^5=R^6=H$, $R^7=$chloro, $R^8=$propyl)

Following the procedure of Example 81(d), but substituting 3-chloro-N-(2,2-dimethylpropionyl)-2-propylaniline for the 2-butyl-3-chloro-N-(2,2-dimethylpropionyl)aniline, the title compound was obtained in 73% yield, m.p. 185°–190°.

Calculated for $C_9H_{12}NCl\cdot HCl$: C, 52.45; H, 6.36; N, 6.80. Found: C, 52.80; H, 6.10; N, 6.81.

d. 2-[(3-Chloro-2-propylphenyl)hydrazono]-2-cyanoacetamide (Formula X, $R^5=R^6=H$, $R^7=$chloro, $R^8=$propyl)

Following the procedure of Example 81(e), but substituting 3-chloro-2-propylaniline hydrochloride for the 2-butyl-3-chloroaniline hydrochloride, the title compound was obtained as a mixture of (E)- and (Z)-isomers in 97% yield, m.p. 175°–182°.

Calculated for $C_{12}H_{13}N_4OCl$: C, 54.44; H, 4.95; N, 21.17. Found: C, 54.35; H, 5.03; N, 21.60.

e. 4-Amino-7-chloro-8-propyl-3-cinnolinecarboxamide (Formula IX, $R^5=R^6=H$, $R^7=$chloro, $R^8=$propyl)

Following the procedure of Example 81(f), but substituting 2-[(3-chloro-2-propylphenyl)hydrazono]-2-cyanoacetamide for the 2-[(2-butyl-3-chlorophenyl)hydrazono]-2-cyanoacetamide, the title compound was obtained in 89% yield, m.p. 252°–254°.

Calculated for $C_{12}H_{13}N_4OCl$: C, 54.44; H, 4.95; N, 21.17. Found: C, 54.65; H, 5.20; N, 21.08.

f. 4-Amino-7-chloro-8-propyl-3-cinnolinecarboxylic acid (Formula VI, $R^5=R^6=H$, $R^7=$chloro, $R^8=$propyl, A=COOH)

Following the procedure of Example 81(g), but substituting 4-amino-7-chloro-8-propyl-3-cinnolinecarboxamide for the 4-amino-8-butyl-7-chloro-3-cinnolinecarboxamide, the title compound was obtained in 86% yield, m.p. 209°–212°.

EXAMPLE 84

4-Amino-7-chloro-N-cyclopropylmethyl-8-propyl-3-cinnolinecarboxamide (Formula I, $R^3=CONRR^9$, $R^4=NH_2$ $R^5=R^6=R=H$, $R^7=$chloro, $R^8=$propyl, $R^9=$cyclopropylmethyl)

Following the procedure of Example 83(a), but substituting (aminomethyl)cyclopropane for the propylamine, the title compound was obtained in 56% yield. Recrystallization from toluene provided an analytical sample, m.p. 176°–178°. $^1$H NMR (CHCl$_3$-d, characteristic peaks only): 0.31 (m, 2H), 0.57 (m, 2H), 1.10 (t, 3H), 7.63 (br. s, 2H) ppm.

Calculated for $C_{16}H_{19}N_4OCl$: C, 60.28; H, 6.01; N, 17.57. Found: C, 60.49; H, 6.02; N, 17.64.

EXAMPLE 85

4-(Butylamino)-N,8-dipropyl-3-cinnolinecarboxamide hydrochloride monohydrate (Formula I, $R^3=CONRR^9$, $R^4=NR^{12}R^{13}$, $R^5=R^6=R^7=R^{13}=R=H$, $R^8=R^9$, =propyl, $R^{12}$=butyl, hydrochloride salt monohydrate)

A reaction flask was charged with sodium hydride (0.186 g of a 50% by weight dispersion in mineral oil) and purged with argon. The sodium hydride dispersion was washed with dry hexane and this hexane wash was discarded. Dry DMF (25 ml) was then added, and the suspension was stirred at 0° while a portion of the product of Example 24 (1.0 g) was added. After gas evolution had ceased, the mixture was warmed to room temperature and 1-iodobutane (0.81 g) was added. After stirring overnight, the reaction mixture was diluted with ethyl acetate (100 ml), and washed with three portions of water (100 ml each). After washing with brine, the organic layer was dried (MgSO$_4$), and evaporated to afford an orange oil. This crude product was purified by chromatography over silica gel using hexane/ethyl acetate (3:1) as the eluting solvent. The appropriate fractions were combined and evaporated to afford an oil which was dissolved in ethyl ether. An ethereal solution of hydrogen chloride was added until no further precipitate appeared. After cooling to 0°, the precipitated solid was collected by filtration, washed with ethyl ether, and dried in vacuo. There was thus obtained 0.70 grams (52% yield) of the title compound as a beige solid, m.p. 160°–165°. $^1$H NMR (DMSO-d$_6$, characteristic peaks only): 0.93 (t, 3H), 0.95 (t, 3H), 0.98 (t, 3H), 3.14 (t, 2H), 3.31 (d of t, 2H), 9.14 (t, exchangeable, 1H) ppm.

Calculated for $C_{19}H_{28}N_4O \cdot HCl \cdot H_2O$: C, 59.59; H, 8.16; N, 14.63. Found: C, 60.06; H, 8.37; N, 15.02.

EXAMPLE 86

N-Cyclopropylmethyl-4-(cyclopropylmethylamino)-8-propyl-3-cinnolinecarboxamide (Formula I, $R^3$=CONRR$^9$, $R^4$=NR$^{12}$R$^{13}$, $R^5=R^6=R^7=R^{13}=R=H$, $R^8$=propyl, $R^9=R^{12}$=cyclopropylmethyl)

A reaction flask was charged with sodium hydride (0.176 g of a 50% by weight dispersion in mineral oil) and purged with nitrogen. To this was added dry DMF (25 ml) and the suspension was stirred at 0° while a portion of the product of Example 66 (1.0 g) was added. After gas evolution had ceased, the mixture was warmed to room temperature and (bromomethyl)cyclopropane (0.45 g) was added. The mixture was stirred for 2.5 days under nitrogen, and then diluted with ethyl acetate (50 ml). The organic phase was washed with three portions of water (75 ml each), and then with brine (75 ml), before drying (Na$_2$SO$_4$) and evaporation to an amber oil. This crude product was purified by chromatography over flash silica gel, using hexane/ethyl acetate (4:1) as the eluting solvent. The appropriate fractions were combined and evaporated to afford a solid which was recrystallized from hexane to afford 0.50 grams (44% yield based on (bromomethyl)cyclopropane) of the title product as fine pale yellow needles, m.p. 61.5°–64.5°. $^1$H NMR (CHCl$_3$-d, characteristic peaks only): 0.29 (m, 2H), 0.39 (m, 2H), 0.57 (m, 2H), 0.70 (m, 2H), 1.05 (t, 3H), 3.35 (m, 4H), 3.68 (m, 2H), 8.76 (t, exchangeable, 1H) ppm.

Calculated for $C_{20}H_{26}N_4O$: C, 70.98; H, 7.74; N, 16.55. Found: C, 70.66; H, 7.66; N, 16.40.

EXAMPLE 87

8-Butyl-N-cyclopropylmethyl-4-(cyclopropylmethylamino)-3-cinnolinecarboxamide (Formula I, $R^3$=CONRR$^9$, $R^4$=NR$^{12}$R$^{13}$, $R^5=R^6=R^7=R^{13}=R=H$, $R^8$=butyl, $R^9=R^{12}$=cyclopropylmethyl)

A reaction flask was charged with sodium hydride (0.322 g of a 50% by weight dispersion in mineral oil) and purged with nitrogen. To this was added dry DMF (40 ml) and the suspension was stirred at room temperature while a portion of the product of Example 64 (2.0 g) was added with stirring. After gas evolution had ceased, (bromomethyl)cyclopropane (1.09 g) was added and the mixture was stirred at room temperature overnight. Ethyl acetate (100 ml) was then added, and the organic layer was washed with three portions of water (100 ml) each, and then with brine (100 ml) before drying (MgSO$_4$) and evaporation to afford an orange oil. This crude product was purified by chromatography over flash silica gel, eluting with hexane/ethyl acetate (9:1). The appropriate fractions were combined and evaporated to afford a solid which was recrystallized from hexane, thus providing 0.70 grams (30% yield) of the title compound as yellow plates, m.p. 73°–75°. Further product could be recovered from the mother liquors of this recrystallization. $^1$H NMR (CHCl$_3$-d, characteristic peaks only): 0.29 (m, 2H), 0.39 (m, 2H), 0.57 (m, 2H), 0.70 (m, 2H), 0.96 (t, 3H), 3.37 (m, 4H), 3.68 (m, 2H), 8.76 (t, exchangeable, 1H) ppm.

Calculated for $C_{21}H_{28}N_4O$: C, 71.56; H, 8.00; N, 15.89. Found: C, 72.03; H, 7.91; N, 15.85.

EXAMPLE 88

8-Butyramido-N-cyclopropylmethyl-8-propyl-3-cinnolinecarboxamide (Formula I, $R^3$=CONRR$^9$, $R^4$=NR$^{12}$R$^{13}$, $R^5=R^6=R^7=R^{13}=R=H$, $R^8$=propyl, $R^9$=cyclopropylmethyl, $R^{12}$=butyryl)

A suspension of sodium hydride (0.371 g of a 50% by weight dispersion in mineral oil) in dry DMF (25 ml) was stirred at room temperature under nitrogen. To this suspension was added dropwise a solution of a portion of the product of Example 66 (2.0 g) in dry DMF (10 ml). After gas evolution had ceased, butyric anhydride (1.27 ml) was added all at once, immediately resulting in a deep orange color. After 30 min, the reaction was quenched by the dropwise addition of water to discharge the deep orange color. It was then poured into water (100 ml) and extracted twice with ethyl ether (100 ml portions each). The combined ether extracts were washed twice with water (100 ml each) and twice with brine (100 ml each) before drying (MgSO$_4$) and evaporation to afford a yellow oil. This crude product was purified by dissolution in ethyl ether/ethyl acetate (1:1) and evaporation onto flash silica gel (50 g). This material was placed atop a column of additional flash silica gel (300 g) in hexane/ethyl ether (9:1) and was eluted with hexane/ethyl ether (9:1, 1 liter), hexane/ethyl ether (8:2, 1 liter), and hexane/ethyl ether (7:3, 1.5 liters) in succession. Fractions of 100 ml were collected; those numbered 18–25 contained the desired product, while later fractions contained unreacted starting material. Evaporation of fractions 18–25 provided 0.54 gram of the title compound (22% yield) as an off-white solid. Recrystallization from ethyl ether/hexane (1:1) provided an analytical sample of slightly yellowish crystals, m.p. 123°–124°. $^1$H NMR (CHCl$_3$-d, characteristic peaks only): 0.33 (m, 2H), 0.61 (m, 2H), 1.07 (t, 3H), 1.08 (t, 3H), 2.62 (t, 2H), 3.42 (m, 4H), 8.93 (t, exchangeable, 1H) ppm.

Calculated for $C_{20}H_{26}N_4O_2$: C, 67.77; H, 7.39; N, 15.81. Found: C, 67.97; H, 7.47; N, 15.88.

EXAMPLE 89 a. 4-Amino-8-iodo-N-propyl-3-cinnolinecarboxamide (Formula I, $R^3$=CONRR$^9$, $R^4$=NH$_2$, $R^5$=$R^6$=$R^7$=R=H, $R^8$=iodo, $R^9$=propyl)

A modified procedure for obtaining the product of Example 36(a) in increased yield and purity is as follows. To a suspension of 2-[(2-iodophenyl)hydrazono]-2-cyano-N-propylacetamide in dry toluene (625 ml) was added anhydrous aluminum chloride (34.40 g) and the mixture was stirred under nitrogen at 60° for 6 hours, then at 45° for 16 hours. The mixture was then cooled to room temperature and diluted with ethyl acetate (600 ml). Using external cooling as necessary to maintain an internal temperature below 35°, water was added dropwise with vigorous stirring until the orange color was fully discharged. After cooling to 10°, an aqueous solution of sodium hydroxide (400 ml of 20% w/v solution) was added and the resulting suspension was stirred for one hour. The phases were separated, and the aqueous layer was stirred with additional ethyl acetate (300 ml). The phases were again separated and the process was repeated. All three organic extracts thus obtained were combined, washed with an equal volume of water, dried (MgSO$_4$), and evaporated to afford a brown solid. This material was triturated with ice-cold ethyl acetate to provide a solid which was recrystallized from methanol/water. After drying over phosphorus pentoxide in vacuo at room temperature, there was obtained 12.88 grams of the title compound. The mother liquors from this recrystallization and the ethyl acetate layer from the trituration described above were combined, evaporated, and redissolved in dichloromethane (100 ml). This dichloromethane solution was stirred with flash silica gel (100 g), and the resulting slurry was poured atop a column of additional flash silica gel (300 g) in dichloromethane. The column was eluted with dichloro-methane (3.5 liters), and then with dichloromethane/acetonitrile (19:1 v/v): the final 2.5 liters of this eluate were evaporated to afford the desired product. This material was recrystallized from methanol/water to provide 15.08 grams (total yield 27.96 g, 76% of theory) of the title compound as a white felt-like solid, m.p. 196.5°-197.5°. $^1$H NMR (CHCl$_3$-d, characteristic peaks only): 1.03 (t, 3H), 1.69 (d of q, 2H), 3.48 (d of t, 2H), 8.59 (br. t, exchangeable, 1H) ppm.

Calculated for: C$_{12}$H$_{13}$N$_4$OI: C, 40.47; H, 3.68; N, 15.73. Found: C, 40.28; H, 3.70; N, 15.72.

b. 2-[(2-Iodophenyl)hydrazono]-2-cyano-N-propylacetamide (Formula VIII, $R^5$=$R^6$=$R^7$=R=H, $R^8$=iodo, $R^9$=propyl)

Commercially available 2-iodoaniline was purified by dissolution in ethyl ether, filtration through a plug of silica gel, and evaporation to dryness. To a solution of this purified material (27.2 g) in glacial acetic acid (74 ml) was added water (37 ml) and the mixture was warmed gently to dissolve any solid. To this mixture was added concentrated hydrochloric acid (37 ml) and the solution was stirred vigorously while cooling on ice to produce a fine white precipitate. Using external cooling as necessary to maintain an internal temperature between 0° and 5°, a solution of sodium nitrite (9.5 g) in water (44 ml) was added dropwise, resulting in a clear light brown solution free of solids. After 15 min this solution was poured all at once into a waiting solution of 2-cyano-N-propylacetamide (17.21 g) in a mixture of ethanol (413 ml) and water (827 ml) containing sodium acetate (165 g) prechilled to −5°. The resulting yellow solution was protected from light and stirred at 0° for 2 days, during which time the product deposited as a thick yellow precipitate. After warming to room temperature, the mixture was diluted with water (800 ml), and the product was collected by filtration. After washing twice with water (400 ml each) and drying in vacuo at room temperature over phosphorus pentoxide, 44.6 grams of yellow solid remained. This crude product was purified by recrystallization from boiling ethyl acetate (1300 ml) to provide bright yellow needles which were washed with hexane and dried in vacuo at room temperature, with protection from light. There was thus obtained 36.88 grams of the title compound (83.5% of theory), m.p. 188.5°-190.5°, identical in all other respects to the product of Example 36(b).

EXAMPLE 90

4-Amino-8-(3-pentynyl)-N-propyl-3-cinnolinecarboxamide (Formula I, $R^3$=CONRR$^9$, $R^4$=NH$_2$, $R^5$=$R^6$=$R^7$=R=H, $R^8$=3-pentynyl, $R^9$=propyl)

A suspension of magnesium turnings (0.72 g) in dry THF (80 ml) was stirred at 0° under nitrogen while 1-bromo-3-pentyne (4.4 g) was added. The mixture was allowed to stir for two hours, and the resulting solution of 3-pentynylmagnesium bromide was transferred by cannula away from any unreacted magnesium into a waiting solution of anhydrous (dried overnight in vacuo at 180°) zinc chloride in dry THF (40 ml). This mixture was stirred at 0° under nitrogen for 30 min. A catalytic amount (0.125 g) of dichloro-[1,1'-bis(diphenylphosphino)ferrocene]palladium(II) (prepared according to the procedure of T. Hayashi, et al., *J. Amer. Chem. Soc.*, (1984) 106:158) was then added, along with a portion of the product of Example 89(a) (1.07 g). After stirring at room temperature overnight, the reaction mixture was diluted with ethyl acetate (200 ml). The resulting slurry was poured into 100 ml of 10% (w/v) HCl solution and this mixture was stirred for 10 min. The phases were separated, and the organic phase was extracted with an additional 50 ml of 10% (w/v) HCl. The combined aqueous layers were washed with an additional volume of ethyl acetate, and the organic phases were discarded. Upon addition of 20% (w/v) sodium hydroxide solution until basic, the aqueous layer was extracted with several volumes of ethyl acetate. This organic phase was washed with 10% (w/v) sodium hydroxide, water, and brine in succession, and was finally dried (MgSO$_4$) and filtered through a plug of silica gel atop of bed of diatomaceous earth. Evaporation of the solvent provided an oil which was purified by chromatography over flash silica gel, eluting with hexane/ethyl acetate (3:1 v/v). Appropriate fractions were combined and evaporated to produce the title compound as a white solid (0.79 g, 45% yield). An analytical sample was obtained by recrystallization from methanol/water, m.p. 119°-120.5°. $^1$H NMR (CHCl$_3$-d, characteristic peaks only): 1.03 (t, 3H), 1.74 (t, 3H), 2.71 (t of q, 2H), 3.48 (d of t, 2H), 3.57 (t, 2H), 8.60 (br. t, exchangeable, 1H) ppm.

Calculated for C$_{17}$H$_{20}$N$_4$O: C, 68.90; H, 6.80; N, 18.84. Found: C, 68.72; H, 6.85; N, 18.84.

EXAMPLE 91

4-Amino-8-cyclopropyl-N-propyl-3-cinnolinecarboxamide (Formula I, $R^3$=CONRR$^9$, $R^4$=NH$_2$, $R^5$=$R^6$=$R^7$=R=H, $R^8$=cyclopropyl, $R^9$=propyl)

Following the procedure of Example 90, but substituting cyclopropyl bromide for 1-bromo-3-pentyne, the title compound was obtained in 88% yield. An analytical sample was prepared by recrystallization from toluene, m.p. 153°–155°. $^1$H NMR (CHCl$_3$-d, characteristic peaks only): 0.90 (m, 2H), 1.03 (t, 3H), 1.23 (m, 2H), 3.37 (m, 1H), 3.49 (d of t, 2H), 8.60 (br. t, exchangeable, 1H) ppm.

Calculated for C$_{15}$H$_{18}$N$_4$O: C, 66.65; H, 6.71; N, 20.72. Found: C, 66.80; H, 6.69; N, 20.73.

EXAMPLE 92

4-Amino-8-phenyl-N-propyl-3-cinnolinecarboxamide (Formula I, R$^3$=CONRR$^9$, R$^4$=NH$_2$, R$^5$=R$^6$=R$^7$=R=H R$^8$=phenyl, R$^9$=propyl)

Following the procedure of Example 90, but substituting a commercially available solution of phenylmagnesium chloride in THF for the solution of 3-pentynylmagnesium bromide in THF, the title compound was obtained in 69% yield as a white solid. An analytical sample was prepared by recrystallization from toluene/hexane; the resulting white crystals, m.p. 115°–117°, contained 1/10 equivalent of residual toluene even after drying in vacuo. $^1$H NMR (CHCl$_3$-d, characteristic peaks only): 1.00 (t, 3H), 3.46 (d of t, 2H), 7.40–7.54 (m, 3H), 7.68–7.88 (m, 5H), 8.60 (br. t, exchangeable, 1H) ppm.

Calculated for C$_{18}$H$_{18}$N$_4$O.1/10 toluene: C, 71.17; H, 6.00; N, 17.75. Found: C, 71.30; H, 6.04; N, 17.65.

EXAMPLE 93

4-Amino-8-phenylmethyl-N-propyl-3-cinnolinecarboxamide (Formula I, R$^3$=CONRR$^9$, R$^4$=NH$_2$, R$^5$=R$^6$=R$^7$=R=H, R$^8$=phenylmethyl, R$^9$=propyl)

Following the procedure of Example 90, but substituting a commercially available solution of benzylmagnesium chloride in THF for the solution of 3-pentynylmagnesium bromide in THF, the title compound was obtained in 47% yield. An analytical sample was prepared by recrystallization from toluene/hexane; the resulting white crystals, m.p. 176°–177°, contained 1/10 equivalent of toluene even after drying in vacuo. $^1$H NMR (CHCl$_3$-d, characteristic peaks only): 1.03 (t, 3H), 3.48 (d of t, 2H), 4.83 (s, 2H), 8.58 (br. t, exchangeable, 1H) ppm.

Calculated for C$_{19}$H$_{20}$N$_4$O. 1/10 toluene: C, 71.79; H, 6.36; N, 16.99. Found: C, 71.93; H, 6.39; N, 16.99.

EXAMPLE 94

4-Amino-8-(3-methylbutyl)-N-propyl-3-cinnolinecarboxamide hydrochloride 3/4 hydrate (Formula I, R$^3$=CONRR$^9$, R$^4$=NH$_2$, R$^5$=R$^6$=R$^7$=R=H, R$^8$=3-methylbutyl, R$^9$=propyl, hydrochloride salt 3/4 hydrate)

Following the procedure of Example 90, but substituting 1-bromo-3-methylbutane for the 1-bromo-3-pentyne, the free base form of the title compound was obtained in 55% yield as a white solid. A portion of this material was dissolved in ethyl ether, filtered, and the filtrate was treated with an ethereal solution of hydrogen chloride until no further product precipitated. This material was collected by filtration and dried in vacuo to provide an analytical sample of the title compound as a pale yellowish powder, m.p. 209°–210°. $^1$H NMR (DMSO-d$_6$, characteristic peaks only): 0.93 (t, 3H), 0.96 (d, 6H), 3.21 (t, 2H), 3.34 (d of t, 2H), 8.99 (br. t, exchangeable, 1H) ppm.

Calculated for C$_{17}$H$_{24}$N$_4$O.HCl. 3/4 H$_2$O: C, 58.27; H, 7.62; N, 15.99. Found C, 58.49; H, 7.49; N, 16.05.

EXAMPLE 95

4-Amino-8-(2-methylpropyl)-N-propyl-3-cinnolinecarboxamide hydrochloride monohydrate (Formula I, R$^3$=CONRR$^9$, R$^4$=NH$_2$, R$^5$=R$^6$=R$^7$=R=H, R$^8$=2-methylpropyl, R$^9$=propyl, hydrochloride salt monohydrate)

Following the procedure of Example 90, but substituting 1-bromo-2-methylpropane for the 1-bromo-3-pentyne, the free base form of the title compound was obtained in 17% yield as a white solid. A portion of this material was dissolved in ethyl ether and an ethereal solution of hydrogen chloride was added until no further precipitate formed. This material was collected by filtration and dried in vacuo to provide an analytical sample of the title compound as a white powder, m.p. 209°–214°. $^1$H NMR (DMSO-d$_6$, characteristic peaks only): 0.91 (d, 6H), 0.92 (t, 3H), 3.09 (d, 2H), 3.33 (d of t, 2H), 8.98 (br. t, exchangeable, 1H) ppm.

Calculated for C$_{16}$H$_{22}$N$_4$O.HCl.H$_2$O: C, 56.38; H, 7.39; N, 16.43. Found: C, 56.29; H, 7.28; N, 16.48.

EXAMPLE 96

4-Amino-8-cyclopentylmethyl-N-propyl-3-cinnolinecarboxamide hydrochloride monohydrate (Formula I, R$^3$=CONRR$^9$, R$^4$=NH$_2$, R$^5$=R$^6$=R$^7$=R=H, R$^8$=cyclopentylmethyl, R$^9$=propyl, hydrochloride salt monohydrate)

Following the procedure of Example 90, but substituting (bromomethyl)cyclopentane for the 1-bromo-3-pentyne, the free base form of the title compound was obtained in 16% yield as a white solid. A portion of this material was dissolved in ethyl ether, and the solution was treated with an ethereal solution of hydrogen chloride until no further precipitate formed. This precipitate was collected and dried in vacuo to provide an analytical sample of the title compound as a white powder, m.p. 210°–214°. $^1$H NMR (DMSO-d$_6$, characteristic peaks only): 0.92 (t, 3H), 3.22 (d, 2H), 3.33 (d of t, 2H), 8.98 (br. t, exchangeable, 1H) ppm.

Calculated for C$_{18}$H$_{24}$N$_4$O.HCl.H$_2$O: C,58.93; H, 7.42; N, 15.27. Found: C, 58.94; H, 7.25; N, 15.24.

(Bromomethyl)cyclopentane was obtained by the following procedure. A solution of commercially available cyclopentanemethanol (20 g) in dry pyridine (220 ml) was stirred at 0° while 4-toluenesulfonyl chloride (42 g) was added. The mixture was stirred at 0° for two hours, and was then held without stirring at 4° overnight. It was then poured into water and the product was extracted into dichloromethane. The dichloromethane extract was washed with 10% (w/v) HCl solution, water, and brine in succession, and was then dried (MgSO$_4$) and evaporated. There was thus obtained the desired intermediate compound, cyclopentylmethyl (4-methylphenyl)sulfonate (44.42 g, 87% yield) as a clear oil. Without further purification, this material was dissolved in dry DMF (175 ml). Lithium bromide (45.5 g) was then added with stirring. The mixture was heated to 45° for three hours, and then cooled to room temperature. The mixture was then diluted with pentane (800 ml), and washed with water (800 ml). The water layer was extracted with an additional portion of pentane (200 ml) and was discarded. The combined pentane layers were washed with water (1000 ml), and brine (200 ml) in succession, and then dried (MgSO$_4$). The solvent was distilled away at atmospheric pressure, and the residue was then vacuum distilled. The desired (bromomethyl)cyclopentane (23.64 g, 83% yield) was obtained as a colorless mobile oil, distilling at 54°–55° at a pressure of 2000 Pascals (15 Torr).

EXAMPLE 97

4-Amino-8-(3-butenyl)-N-propyl-3-cinnolinecarboxamide (Formula I, $R^3$=CONRR$^9$, $R^4$=NH$_2$, $R^5$=R$^6$=R$^7$=R=H, $R^8$=3-butenyl, $R^9$=propyl)

(3-Butenyl)magnesium bromide was prepared by adding 4-bromo-1-butene (1.02 ml) to magnesium chips (0.253 g) in dry THF (27 ml) and stirring under an atmosphere of argon until most of the magnesium had been consumed. The resulting solution was transferred via cannula into a vigorously-stirred solution of anhydrous (dried overnight in vacuo at 185° C.) zinc chloride (1.39 g) in dry THF (13 ml) under argon; a white precipitate appeared as the addition proceeded. The mixture was stirred at ambient temperature for 5 min. Dichloro[1,1'-bis(diphenylphosphino)ferrocene]palladium(II) (45 mg) and a portion of the product of Example 35(a) (0.318 g) were added and the resultant mixture was stirred for 21.5 hours at ambient temperature under argon. The reaction mixture was poured into saturated aqueous ammonium sulfate (250 ml) and stirred for 5 min. This mixture was extracted twice with ethyl acetate (250 ml each). The combined ethyl acetate extracts were washed successively with water (250 ml) and brine and were then dried (MgSO$_4$). Filtration and evaporation of solvent in vacuo yielded 0.60 g of an olive drab oil, which was purified by flash chromatography over flash silica gel (25 g), eluting with hexanes/ethyl acetate (3:1, v/v) and collecting 25 ml fractions. Fractions numbered 7–12 were combined and evaporated in vacuo to afford the title compound (0.243 g, 83% yield) as a white solid.

Using material from another repetition of this method, an analytical sample was obtained by recrystallization from toluene, providing an off-white powder, m.p. 116°–117.5°. $^1$H NMR (CHCl$_3$-d, characteristic peaks only): 1.03 (t, 3H), 4.95–5.09 (m, 2H), 5.93 (m, 1H) ppm.

Calculated for C$_{16}$H$_{20}$N$_4$O: C, 67.58; H, 7.09; N, 19.70. Found: C, 67.87; H, 7.18; N, 19.84.

EXAMPLE 98 a. 4-Amino-8-(3-hydroxybutyl)-N-propyl-3-cinnolinecarboxamide (Formula I, $R^3$=CONRR$^9$, $R^4$=NH$_2$, $R^5$=R$^6$=R$^7$=R=H, $R^8$=3-hydroxybutyl, $R^9$=propyl)

A mixture of 4-amino-8-[3-(tert-butyldimethylsiloxy)butyl]-N-propyl-3-cinnolinecarboxamide (0.566 g), acetonitrile (19 ml), and 50% aqueous hydrofluoric acid (1 ml) was stirred at ambient temperature for 2 hours. This mixture was poured into saturated aqueous sodium bicarbonate (100 ml) and extracted with ethyl acetate (100 ml). The ethyl acetate extract was washed with brine (50 ml) and dried (MgSO$_4$) Filtration and evaporation of solvent yielded the title compound (0.392 g, 95% yield) as an off-white solid. An analytical sample was obtained as follows. A portion of this material was purified by flash chromatography over silica gel, eluting the desired product with hexanes/ethyl acetate (1:1 v/v). Evaporation of the appropriate fractions provided a white powder, m.p. 123°–124°. $^1$H NMR (CHCl$_3$-d, characteristic peaks only): 1.03 (t, 3H), 1.18 (d, 3H), 3.55 (m, 1H) ppm.

Calculated for C$_{16}$H$_{22}$N$_4$O$_2$: C, 63.56; H, 7.33; N, 18.53. Found: C, 63.65; H, 7.34; N, 18.50.

b. 4-Amino-8-[3-(tert-butyldimethylsiloxy)butyl]-N-propyl-3-cinnolinecarboxamide (Formula I, $R^3$=CONRR$^9$, $R^4$=NH$_2$, $R^5$=R$^6$=R$^7$=R=H, $R^8$=3-(tert-butyldimethylsiloxy)butyl, $R^9$=propyl)

3-(tert-Butyldimethylsiloxy)butylmagnesium bromide was prepared by adding 1-bromo-3-(tert-butyldimethylsiloxy)butane (15.55 g: prepared as described by H. Gerlach et al., *Helv. Chim. Acta*, (1977) 60:2860) to magnesium chips (1.55 g) in dry THF (50 ml) and stirring at ambient temperature under an atmosphere of argon for 2 hours, resulting in the formation of a voluminous white precipitate. This precipitate was dissolved by adding an additional 50 ml of dry THF and the solution was refluxed for 30 min. After cooling to ambient temperature, this solution was transferred via cannula into a vigorously stirred solution of anhydrous (dried overnight in vacuo at 150°) zinc chloride (9.45 g) in dry THF (80 ml) under argon; a white precipitate appeared as the addition proceeded. An additional 30 ml of dry THF was used to wash the residual organomagnesium reagent into the zinc chloride solution. This mixture was stirred at ambient temperature for 15 min. Dichloro[1,1'-bis(diphenylphosphino)ferrocene]palladium(II) (0.305 g) and a portion of the product of Example 35(a) (1.95 g) were added and the resultant mixture was refluxed for 41 hours. After cooling, the reaction mixture was poured into a mixture of saturated aqueous ammonium sulfate (750 ml) and water (250 ml) and stirred for 15 min. This mixture was extracted twice with ethyl acetate (750 ml each). The combined ethyl acetate extracts were washed with water (500 ml) and brine (500 ml) in succession. After drying (MgSO$_4$), filtration and evaporation of solvent in vacuo yielded 7.00 g of reddish-brown oil, which was purified by flash chromatography over flash silica gel (200 g), by eluting with hexanes-ethyl acetate (4:1, v/v) and collecting 125 ml fractions. Fractions numbered 10–16 were combined and evaporated in vacuo to afford the title compound (2.18 g, 83% yield) as a cream-colored powder, m.p. 106°–108°. $^1$H NMR (CHCl$_3$-d, characteristic peaks only): 0.08 (s, 3H), 0.09 (s, 3H), 0.93 (s, 9H), 1.03 (t, 3H), 1.21 (d, 3H), 4.00 (m, 1H) ppm.

Calculated for C$_{22}$H$_{36}$N$_4$O$_2$Si: C, 63.42; H, 8.71; N, 13.45. Found: C, 63.55; H, 8.73; N, 13.41.

EXAMPLE A

| Tablets | |
|---|---|
| Each tablet contains | |
| 4-Amino-8-butyl-N—cyclopropylmethyl-3-cinnoline carboxamide | 5 mg |
| Lactose | 88 mg |
| Magnesium stearate | 1 mg |
| Polyvinylpyrrolidone | 2 mg |
| Sodium starch glycollate | 4 mg |

The lactose, sodium starch glycollate and polyvinylpyrrolidone are mixed in a planetary mixer and water added until a suitable mass for granulation is obtained. The mass obtained is granulated through a suitable size mesh and dried to obtain the optimum moisture content. The magnesium stearate is then added and the dry granulate is then passed through a further screen before final blending and compression to yield tablets each weighing 100 mg.

EXAMPLE B

| Tablets | |
|---|---|
| Each tablet contains | |
| 4-Amino-8-butyl-N—cyclopropylmethyl-3-cinnoline carboxamide | 250 mg |
| Lactose | 122 mg |
| Magnesium stearate | 4 mg |
| Polyvinylpyrrolidone | 8 mg |
| Sodium starch glycollate | 16 mg |

The tablets are formuled as described in Example A to yield tablets each weighing 600 mg.

EXAMPLE C

| Tablets | |
|---|---|
| Each tablet contains | |
| 4-Amino-8-butyl-N—cyclopropylmethyl-3-cinnoline carboxamide | 100 mg |
| Lactose | 86 mg |
| Magnesium stearate | 2 mg |
| Polyvinylpyrrolidone | 4 mg |
| Sodium starch glycollate | 8 mg |

The tablets are formulated as described in Example A to yield tablets each weighing 200 mg.

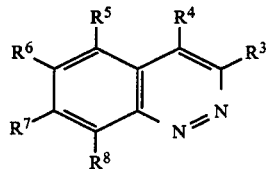 I

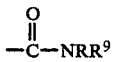 II

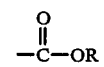 III

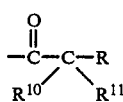 IV

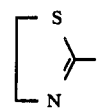 V

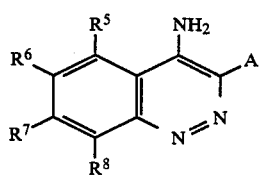 VI

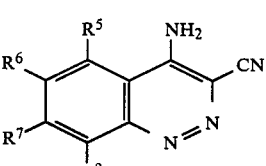 VII

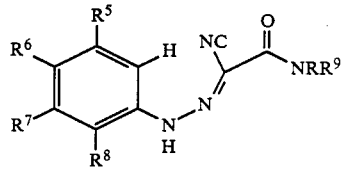 VIII

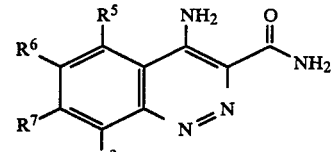 IX

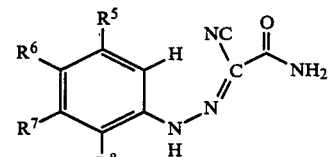 X

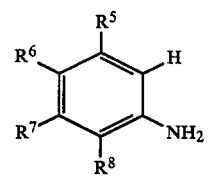 XI

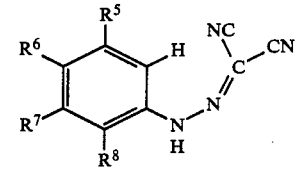 XII

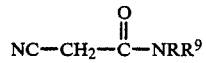 XIII

What is claimed is:

1. A compound of formula I

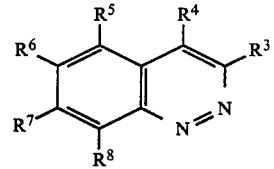 I wherein

R$^3$ is selected from a group consisting of an amide of formula CONRR$^9$ and a ketone of formula COCRR$^{10}$R$^{11}$;

R$^4$ is selected from a group consisting of —NR$^{12}$R$^{13}$ and OH;

R$^5$, R$^6$ and R$^7$ are each independently selected from a group consisting of hydrogen, (1–5C)alkyl, chloro and methoxy;

R$^8$ is selected from a group consisting of (1–5C)alkyl, (2–4C)alkenyl, (2–5C)alkenyl, (3–6C)cycloalkyl, (4–7C)cycloalkylalkyl, phenylmethyl, and (1–4C)hydroxyalkyl;

R and R$^9$ are each independently selected from a group consisting of hydrogen (provided that R and $R^9$ cannot both be hydrogen at the same time), (1–4C)alkyl, (3–4C)alkenyl, (3–4C)alkenyl, (4–5C)cycloalkylalkyl, (2–4C)fluor alkyl having 1–4 fluoros provided that no fluorine is on a carbon bonded to nitrogen, 4, 5-dihydrothiazol-2-yl, phenylmethyl, or R and $R^9$, when taken together, form a (4–5C)alkylene in which one of the carbons may optionally be replaced by an oxygen, or, when taken together, form a 4 carbon alkenylene;

$R^{10}$ and $R^{11}$ are each hydrogen;

$R^{12}$ and $R^{13}$ are each independently selected from a group consisting of hydrogen, (1–4C)alkyl, (4–6C)cycloalkylalkyl and (2–4C)acyl;

or a pharmaceutically acceptable salt thereof.

2. A compound as claimed in claim 1 wherein $R^5$ is hydrogen or chloro; $R^6$ is hydrogen, chloro, methoxy or butyl; $R^7$ is hydrogen, chloro, methyl, methoxy or pentyl; $R^8$ is methyl, ethyl, propyl, butyl, pentyl, cyclopropyl, 2-methylpropyl, 3-methylbutyl, cyclopentylmethyl, 3-butenyl, 3-hydroxybutyl, phenylmethyl or 3-pentynyl; R is hydrogen, methyl, ethyl, propyl, butyl, cyclopropylmethyl, 2-propenyl or phenylmethyl; $R^9$ is methyl, ethyl, propyl, butyl, 2-methylpropyl, cyclopropylmethyl, cyclobutylmethyl, 2-propenyl, 2-propynyl, 2-butynyl, cyclopropyl, 2,2,2-trifluoroethyl, phenylmethyl, 3-hydroxyproyyl, or 4,5-dihydrothiazol-2-yl; $R^{10}$ is hydrogen; and $R^{11}$ is hydrogen.

3. A compound as claimed in claim 1 wherein R is hydrogen; $R^3$ is CONRR$^9$; $R^5$ is hydrogen; $R^6$ is hydrogen; $R^7$ is hydrogen or chloro; $R^8$ is (3–5C)alkyl; and $R^9$ is (2–4C)alkyl, (3–4C)alkenyl, or (4–5C)(cycloalkyl)alkyl, or a pharmaceutically acceptable salt thereof.

4. A compound as claimed in claim 1 selected from the group consisting of 4-amino-N, 8-dipropyl-3-cinnolinecarboxamide; 4-amino-8-butyl-N-(2-propenyl)-3-cinnolinecarboxamide; 4-amino-8-pent N-(2-propenyl)-3-cinnolinecarboxamide; 4-amino-8-butyl-N-cyclopropylmethyl 3-cinnolinecarboxamide; 4-amino-N-cyclopropylmethyl-8-propyl-3-cinnolinecarboxamide; 4-amino-8-butyl-N-cyclobutylmethyl-3-cinnolinecarboxamide; 4-amino-butyl-N-cyclopropyl-3-cinnolinecarboxamide; 4-amino-8-(3-methylbutyl)-N-propy 3-cinnolinecarboxamide; and 4-amino-8-cyclopentyl-methyl-N-propyl-3-cinnolinecarboxamide; or a pharmaceutically acceptable salt thereof.

5. A compound as claimed in claim 1 wherein said compound is 4-amino-N-cyclopropylmethyl-8-propyl-3-cinnolinecarboxamide or a pharmaceutically acceptable salt thereof.

6. A compound as claimed in claim 1 wherein said compound is 4-amino-8-butyl-N-cyclopropylmethyl-3-cinnolinecarboxamide or a pharmaceutically acceptable salt thereof.

7. A pharmaceutically acceptable salt as claimed in claim 1 wherein said salt is an acid addition salt.

8. A pharmaceutical composition comprising a compound of claim 1 or a pharmaceutically acceptable salt thereof in an amount sufficient to reduce anxiety in a living mammal in need of such treatment in association with a non-toxic pharmaceutically acceptable diluent or carrier.

9. A method of treating anxiety in a living mammal comprising administering to the mammal an effective amount of a compound of claim 1 or a pharmaceutically acceptable salt thereof.

* * * * *

UNITED STATES PATENT AND TRADEMARK OFFICE
CERTIFICATE OF CORRECTION

PATENT NO. : 4,886,800                      Page 1 of 3

DATED : DECEMBER 12, 1989

INVENTOR(S) : JAMES F. RESCH

It is certified that error appears in the above-identified patent and that said Letters Patent is hereby corrected as shown below:

Column 1, line 22, "(1968):" should read --(1968);--.

Column 1, line 25, "(1984):" should read --(1984);--.

Column 2, line 26, "(cycloalkyl)," should read --(cycloalkyl)alkyl,--.

Column 2, line 27, "(v):" should read -- (V),--.

Column 2, line 29, "(2-10C)fluoroaelkyl" should read --(2-10C)fluoroalkyl--.

Column 3, line 2, "above:" should read --above;--.

Column 3, line 27, "(4-6C)alkenylene:" should read --(4-6C)alkenylene;--.

Column 3, line 34, "OH:" should read --OH;--.

Column 3, line 37, "methoxy:" should read --methoxy;--.

Column 3, line 50, "alkenylene:" should read --alkenylene;--.

Column 3, line 51, "hydrogen:" should read --hydrogen;--.

Column 3, line 56, "chloro." should read --chloro;--.

Column 3, line 57, "butyl:" should read --butyl;--.

Column 3, line 58, "pentyl:" should read --pentyl;--.

Column 3, line 64, "phenylmethyl:" should read --phenylmethyl;--.

Column 4, line 1, "hydrogen:" should read --hydrogen;--.

UNITED STATES PATENT AND TRADEMARK OFFICE
CERTIFICATE OF CORRECTION

PATENT NO. : 4,886,800

DATED : DECEMBER 12, 1989

INVENTOR(S) : JAMES F. RESCH

It is certified that error appears in the above-identified patent and that said Letters Patent is hereby corrected as shown below:

Column 4, line 14, "formula II:" should read --formula II;--.

Column 4, line 25, "formula II:" should read --formula II;--.

Column 4, line 26, "$R^5=R^6=R^7=R=H$:" should read --$R^5=R^6=R^7=R=H$;--.

Column 4, line 45, "$R^5=R^6=R^7=R=H$" should read --$R^5=R^6=R^7=R=H$;--.

Column 4, line 48, "formula II:" should read --formula II;--.

Column 13, line 27, "N, 20.6." should read --N, 20.67.--.

Column 14, line 17, "H, 5.87:" should read -- H, 5.87;--.

Column 21, line 37, "reached:" should read --reached;--.

Column 21, line 51, "$C_{15}H_{19}N_3)_2$:" should read --$C_{15}H_{19}N_3O_2$:--.

Column 22, line 45, "$^1$NMR" should read --$^1$H NMR--.

Column 32, line 1, "T.N.:" should read --T.N.;--.

Column 34, line 6, "3.42(br. (br. s, 2H) ppm." should read --3.42 (br. s, 2H), 3.71 (br. s, 2H) ppm.--.

Column 34, line 27, "$C_{16}H_{20}N_4O_2 \cdot HCl$." should read --$C_{16}H_{20}N_4O_2 \cdot HCl$. 1/6 $H_2O$:--.

Column 37, line 63, "$T^8=^9$=propyl" should read --$R^8=R^9$=propyl--.

Column 46, line 8, "(15.55 g:" should read --(15.55 g;--.

Column 49, line 3, "(2-4C)fluor alkyl" should read --(2-4C)fluoroalkyl--.

Column 50, line 9, "4-amino-butyl-N-cyclopropyl-3-cin-" should read --4-amino-8-butyl-N-cyclopropyl-3-cin---.

UNITED STATES PATENT AND TRADEMARK OFFICE
CERTIFICATE OF CORRECTION

PATENT NO. : 4,886,800

DATED : Decmber 12, 1989

INVENTOR(S) : James F. Resch

It is certified that error appears in the above-identified patent and that said Letters Patent is hereby corrected as shown below:

Column 50, line 4, "4-amino-8-pent" should read --4-amino-8-pentyl--.

Signed and Sealed this

Twenty-fifth Day of May, 1993

Attest:

MICHAEL K. KIRK

*Attesting Officer*     Acting Commissioner of Patents and Trademarks